(12) United States Patent
Kramer et al.

(10) Patent No.: US 12,156,886 B2
(45) Date of Patent: *Dec. 3, 2024

(54) METHODS OF INCREASING BLOOD OXYGEN SATURATION

(71) Applicant: ThermoLife International, LLC, Signal Hill, CA (US)

(72) Inventors: Ronald Kramer, Signal Hill, CA (US); Alexandros Nikolaidis, Nea Kallikratia (GR)

(73) Assignee: ThermoLife International, LLC, Signal Hill, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/525,841

(22) Filed: Nov. 12, 2021

(65) Prior Publication Data

US 2022/0143080 A1 May 12, 2022

Related U.S. Application Data

(60) Provisional application No. 63/232,852, filed on Aug. 13, 2021, provisional application No. 63/148,517, filed on Feb. 11, 2021, provisional application No. 63/113,114, filed on Nov. 12, 2020.

(51) Int. Cl.
| | | |
|---|---|---|
| *A61K 33/30* | (2006.01) | |
| *A61K 31/194* | (2006.01) | |
| *A61K 33/00* | (2006.01) | |
| *A61K 33/06* | (2006.01) | |
| *A61P 11/00* | (2006.01) | |
| *A61P 11/06* | (2006.01) | |
| *A61P 31/04* | (2006.01) | |
| *A61P 31/14* | (2006.01) | |

(52) U.S. Cl.
CPC ............ *A61K 33/30* (2013.01); *A61K 31/194* (2013.01); *A61K 33/00* (2013.01); *A61K 33/06* (2013.01); *A61P 11/00* (2018.01); *A61P 11/06* (2018.01); *A61P 31/04* (2018.01); *A61P 31/14* (2018.01)

(58) Field of Classification Search
CPC ...... A61K 33/06; A61K 31/295; A61K 33/30; A61K 33/26; A61K 33/24; A61P 9/08; A61P 11/00; A61P 31/12; A61P 29/00
See application file for complete search history.

(56) References Cited

U.S. PATENT DOCUMENTS

| | | | |
|---|---|---|---|
| 1,916,983 A | 7/1933 | McKee | |
| 2,176,144 A | 10/1939 | Moskowitz | |
| 2,553,533 A | 5/1951 | Komarik | |
| 3,230,036 A | 1/1966 | Kappelmann | |
| 3,552,978 A | 1/1971 | Inklaar | |
| 3,886,040 A | 5/1975 | Chibata | |
| 3,997,659 A | 12/1976 | Knohl | |
| 4,146,611 A | 3/1979 | Ondetti | |
| 4,291,015 A | 9/1981 | Keith | |
| 4,379,177 A | 4/1983 | McCoy | |
| 4,687,782 A | 8/1987 | Brantman | |
| 4,743,614 A | 5/1988 | Terano | |
| 4,749,402 A | 6/1988 | Garrett | |
| 4,871,550 A | 10/1989 | Millman | |
| 4,976,960 A | 12/1990 | Grossman | |
| 4,996,067 A | 2/1991 | Kobayashi | |
| 5,026,071 A | 6/1991 | Miraglia, Jr. | |
| 5,026,721 A | 6/1991 | Dudrick | |
| 5,242,697 A | 9/1993 | Luca | |
| 5,485,827 A * | 1/1996 | Zapol ................. | A61M 15/009 128/200.14 |
| 5,500,436 A | 3/1996 | Schoenafinger | |
| 5,543,430 A | 8/1996 | Kaesemeyer | |
| 5,576,351 A | 11/1996 | Yoshimura | |
| 5,631,031 A | 5/1997 | Meade | |
| 5,679,704 A | 10/1997 | Schoenafinger | |
| 5,767,160 A | 6/1998 | Kaesemeyer | |
| 5,904,924 A | 5/1999 | Gaynor | |
| 5,965,596 A | 10/1999 | Harris | |
| 6,063,432 A | 5/2000 | Maxwell | |
| 6,136,339 A | 10/2000 | Gardiner | |

(Continued)

FOREIGN PATENT DOCUMENTS

| | | |
|---|---|---|
| CN | 1056225 | 11/1991 |
| CN | 1049824 | 3/2000 |

(Continued)

OTHER PUBLICATIONS

Rao, "Pulse oximeters for COVID-19: What oxygen saturation levels can tell you about SARSCoV-2 infection", article obtained from: https://www.healio.com/news/pulmonology/20220127/pulse-oximeter-readings-unreliable-to-assess-covid19-pneumonia-severity-across-ethnicities, obtained on May 13, 2022 (Year: 2020).*

Teragawa et al. (Heart, 86:212-216, 2001) Magnesium causes nitric oxide independent coronary artery vasodilation in humans.

(Continued)

*Primary Examiner* — Nicole P Babson
*Assistant Examiner* — John P Nguyen
(74) *Attorney, Agent, or Firm* — Booth Udall Fuller, PLC; Pacer K. Udall

(57) ABSTRACT

The disclosure is directed to compositions and methods of increasing oxygen saturation (SpO2) in subjects in need thereof as well as alleviating, treating or curing symptoms and conditions associated with lower SpO2 levels (below 95%). The compositions are preferably solid and comprise a nitrate anion source, an elemental metal (uncharged), and optionally an acid. The compositions are preferably administered orally.

41 Claims, 7 Drawing Sheets

(6 of 7 Drawing Sheet(s) Filed in Color)

(56) References Cited

U.S. PATENT DOCUMENTS

| | | |
|---|---|---|
| 6,159,485 A | 12/2000 | Yu |
| 6,172,098 B1 | 1/2001 | Harris |
| 6,277,884 B1 | 8/2001 | De Tejada |
| 6,337,349 B2 | 1/2002 | Scafetta |
| 6,451,341 B1 | 9/2002 | Slaga |
| 6,562,869 B1 | 5/2003 | Hamilton |
| 6,608,109 B2 | 8/2003 | Allen |
| 6,784,209 B1 | 8/2004 | Gardiner |
| 7,235,237 B2 | 6/2007 | Loscalzo |
| 7,777,014 B2 | 8/2010 | Cattaruzza |
| 7,777,074 B2 | 8/2010 | Kramer |
| 7,799,782 B2 | 9/2010 | Munson |
| 8,034,836 B2 | 10/2011 | Kramer |
| 8,048,921 B2 | 11/2011 | Kramer |
| 8,178,572 B2 | 5/2012 | Kramer |
| 8,183,288 B2 | 5/2012 | Kramer |
| 8,455,531 B2 | 6/2013 | Kramer |
| 8,466,187 B2 | 6/2013 | Kramer |
| 8,569,368 B2 | 10/2013 | Kramer |
| 8,569,369 B2 | 10/2013 | Kramer |
| 8,703,719 B1 | 4/2014 | Abraham |
| 8,852,660 B2 | 10/2014 | Miljkovic |
| 8,952,045 B1 | 2/2015 | Kramer |
| 8,952,046 B1 | 2/2015 | Kramer |
| 8,957,100 B1 | 2/2015 | Kramer |
| 8,957,101 B1 | 2/2015 | Kramer |
| 9,180,140 B2 | 11/2015 | Lundberg |
| RE46,372 E | 4/2017 | Miller |
| 10,646,508 B1 | 5/2020 | Kramer |
| 10,736,916 B1 | 8/2020 | Kramer |
| 2001/0002269 A1 | 5/2001 | Zhao |
| 2001/0011074 A1 | 8/2001 | Piccolo |
| 2001/0048952 A1 | 12/2001 | Siskind |
| 2001/0055617 A1 | 12/2001 | Mattern |
| 2001/0056069 A1 | 12/2001 | Klaus |
| 2002/0006532 A1 | 1/2002 | Robin |
| 2002/0065323 A1 | 5/2002 | Crooks |
| 2002/0119933 A1 | 8/2002 | Butler |
| 2002/0147156 A1 | 10/2002 | Petit |
| 2002/0155174 A1* | 10/2002 | Benjamin ............. A01N 59/00 424/718 |
| 2003/0012744 A1 | 1/2003 | Pedersen |
| 2003/0014238 A1 | 1/2003 | Xun |
| 2003/0091615 A1 | 5/2003 | Craig |
| 2003/0097401 A1 | 5/2003 | Bauman |
| 2003/0119888 A1 | 6/2003 | Allen |
| 2003/0139354 A1 | 7/2003 | Buccholz |
| 2004/0006140 A1 | 1/2004 | Kaesemeyer |
| 2004/0048870 A1 | 3/2004 | Amir |
| 2004/0057926 A1 | 3/2004 | Ochoa |
| 2004/0058011 A1 | 3/2004 | Petersson |
| 2004/0087518 A1 | 5/2004 | Verlaan |
| 2004/0097401 A1 | 5/2004 | Datta |
| 2004/0126366 A1 | 7/2004 | Kaddurah-Daouk |
| 2004/0224868 A1* | 11/2004 | Meyerhoff ............. A61K 33/34 510/320 |
| 2004/0242682 A1 | 12/2004 | Kaesemeyer |
| 2005/0043274 A1 | 2/2005 | Murad |
| 2005/0053673 A1 | 3/2005 | Netke |
| 2005/0171194 A1 | 8/2005 | Yu |
| 2005/0196474 A1 | 9/2005 | Anno |
| 2005/0256192 A1 | 11/2005 | Gardiner |
| 2005/0261257 A1 | 11/2005 | Vermeer |
| 2005/0287210 A1 | 12/2005 | Ron |
| 2005/0288372 A1 | 12/2005 | Ron |
| 2005/0288373 A1 | 12/2005 | Ron |
| 2006/0014238 A1 | 1/2006 | Gholap |
| 2006/0018281 A1 | 1/2006 | Sadot |
| 2006/0029668 A1 | 2/2006 | Ron |
| 2006/0063827 A1 | 3/2006 | Yu |
| 2006/0116328 A1 | 6/2006 | Babizhayev |
| 2006/0142382 A1 | 6/2006 | Morimoto |
| 2006/0182815 A1 | 8/2006 | Gladwin |
| 2006/0198899 A1 | 9/2006 | Gardiner |
| 2006/0241181 A1 | 10/2006 | Pola |
| 2006/0275909 A1 | 12/2006 | Spitzer |
| 2007/0037880 A1 | 2/2007 | Mailland |
| 2007/0105817 A1 | 5/2007 | Page |
| 2007/0141174 A1 | 6/2007 | Cornett |
| 2007/0154569 A1 | 7/2007 | Gladwin |
| 2008/0004218 A1 | 1/2008 | Quay |
| 2008/0026075 A1 | 1/2008 | Kondo |
| 2008/0038410 A1* | 2/2008 | Giordano ............. A23L 33/155 426/74 |
| 2008/0138448 A1 | 6/2008 | Heuer |
| 2008/0214649 A1 | 9/2008 | Yu |
| 2008/0233186 A1 | 9/2008 | Romero |
| 2008/0268095 A1 | 10/2008 | Herzog |
| 2009/0076110 A1 | 3/2009 | Kramer |
| 2009/0137670 A1 | 5/2009 | Kramer |
| 2009/0280199 A1 | 11/2009 | Russell |
| 2009/0306208 A1 | 12/2009 | Shimada |
| 2010/0004335 A1 | 1/2010 | Kagami |
| 2010/0047344 A1 | 2/2010 | Lundberg |
| 2010/0092441 A1* | 4/2010 | Lundberg ............. A61K 31/21 423/400 |
| 2010/0172890 A1 | 7/2010 | Gilad |
| 2011/0064712 A1 | 3/2011 | Amato |
| 2011/0123654 A1 | 5/2011 | Jaeger |
| 2012/0220643 A1 | 8/2012 | Kramer |
| 2013/0071494 A1 | 3/2013 | Bryan |
| 2013/0101704 A1 | 4/2013 | Meehan |
| 2015/0246066 A1 | 9/2015 | Nelson |
| 2017/0042935 A1 | 2/2017 | Sakamoto |
| 2017/0303582 A1 | 10/2017 | Lu |
| 2018/0133247 A1 | 5/2018 | Green |
| 2020/0222449 A1* | 7/2020 | Nikolaidis ............. A61K 33/00 |
| 2020/0352986 A1* | 11/2020 | Green ............. A61K 31/375 |
| 2021/0220422 A1 | 7/2021 | Parker |

FOREIGN PATENT DOCUMENTS

| | | |
|---|---|---|
| CN | 1631539 | 6/2005 |
| CN | 20041009958 | 6/2005 |
| EP | 797992 A2 | 1/1997 |
| EP | 1336602 | 8/2003 |
| EP | 1429829 B1 | 11/2013 |
| EP | 2896302 | 7/2015 |
| GB | 1089084 A | 11/1967 |
| GB | 2008578 A | 6/1979 |
| GB | 2052976 A | 2/1981 |
| GB | 2354441 | 3/2001 |
| JP | 2010519335 | 6/2010 |
| JP | 2012529909 | 11/2012 |
| JP | 2014513527 | 6/2014 |
| JP | 2014122162 | 7/2014 |
| KR | 20110015141 A | 2/2011 |
| WO | 9843499 | 10/1998 |
| WO | 0040217 | 7/2000 |
| WO | 0117525 | 3/2001 |
| WO | 0195897 | 12/2001 |
| WO | 03063789 A2 | 8/2003 |
| WO | 2005062713 | 7/2005 |
| WO | 2005115175 | 12/2005 |
| WO | 2005115175 A1 | 12/2005 |
| WO | 2006025286 | 3/2006 |
| WO | 2006124161 | 11/2006 |
| WO | 2007000985 | 1/2007 |
| WO | 2007066642 | 6/2007 |
| WO | 2007093808 | 8/2007 |
| WO | 2008009615 A1 | 1/2008 |
| WO | 2008043855 | 4/2008 |
| WO | 2008105730 | 9/2008 |
| WO | 2008105731 | 9/2008 |
| WO | 2018019663 | 2/2018 |
| WO | 2020160509 A1 | 8/2020 |
| WO | 2020214841 A1 | 10/2020 |
| WO | 2021188163 | 9/2021 |

OTHER PUBLICATIONS

ATSDR Case Studies in Environmental Medicine Nitrate/Nitrite Toxicity published by the U.S. Department of Health and Human Services on Dec. 5, 2013. ATSDR Case Studies in Environmental Medicine Nitrate/Nitrite Toxicity.

(56) References Cited

OTHER PUBLICATIONS

Kouzenkov V.S. et al. Sodium potassium effect on development of nerological deficiency in experimental model of 1 brain ishemia), non-official translation (Moscow University Bulletin Ser. 16. Biology. 2014, No. 4, pp. 9-14), p. 9, p. 10, col. 1, paragraph 3—col. 2, paragraph 3, p. 12, col. 2, paragraph 2—p. 13, col. 1, paragraph 1, figs. 1-4.

Professor of Udinsev. Nitrates and physical performance. Siberian fiber. Aug. 9, 2018. [on-line] [ retrieved on 2 p/29/2020] (Retrieved from the Internet: https://tfzp.ru/zdorovyj-obraz-zhizni/v/nitraty/nitraty-i-fizicheskaya-abotosposobnosto, p. 2, paragraph 2—p. 3, paragraph 1, p. 4, paragraph 1.

A. Patrician et al., "Dietary nitrate enhances arterial oxygen saturation after dynamic apnea", Scand J Med Sci Sports, (20170000), vol. 27, doi: 10.1111/sms.12684, pp. 622-626, XP055943939.

Acetyl/propionyl Carnitine from BodyBuilding, 2006. 1 page.

Arnold et al. (Biochemistry 99;38(15):4750-4756) (Year: 1999) 7 pages.

Curry, M.D., Steven, "Methemoglobinemia", Ann Emerg Med, 11, 214-221, 1982.

Dymatize® Xpand 2x®, Fruit Punch, Dymatize GNC, www.gnc.com/product/index.jsp?productId=13180805, Jun. 13, 2013. 4 pages.

Ekblom et al, The New England Journal of medicine, 2006, 335; 26, pp. 2792-2793.

Gago et al., Red wine-dependent reduction of nitrite to nitric oxide in the stomach, Free Radical Biology and Medicine 43:1233-1242, 2007. 10 pages.

George Barger, M.A., D.Sc., "The Simpler Natural Bases", Monographs on Biochemistry, U.C.D. Library, Nov. 23, 1960, Digitized 2007. 232 pages.

Gonzalez, "Migraines Are Correlated with Higher Levels of Nitrate-, Nitrite-, and Nitric Oxide-Reducing Oral Microbes in the American Gut Project Cohort". mSystems. Oct. 18, 2016;1(5):e00105-16. doi: 10.1128/mSystems.00105-16. Erratum in: mSystems. ( Year: 2016).

Gwartney, "On the Horizon: A Glimpse into the Future of Supplementation," in Pump magazine, (Year: Nov./Dec. 1998) 4 pages.

H. Yamasaki, "Blood nitrate and nitrite modulating nitric oxide bioavailability: potential therapeutic functions in COVID-19", Nitric Oxide, vol. 103, doi:https://doi.org/10.1016/j.niox. 2020.07.00 5, (Jul. 23, 2020), pp. 29-30, XP055943941.

Mirvish, SS (Annals of New York Academy of Sciences. 1975; pp. 175-180) (Year: 1975).

Qin, Yu, et al., "Portable Nitric Oxide (NO) Generator Based on Electrochemical Reduction of Nitrite for Potential Applications in Inhaled NO Therapy and Cardiopulmonary Bypass Surgery", Mol Pharmaceutics, http://pubs.acs.org, 37 pages, 2017.

Shinbo, Toshihiro, et al., "Breathing nitric oxide plus hydrogen gas reduces ischemia-reperfusion injury and nitrotyrosine production in murine heart", Am J Physiol Heart Circ Physiol, 305, H542-H550, 2013.

Sulcius, A. (J. Chem. Educ. 2015;92:1971-1972). (Year: 2015) 6 pages.

Mostad et al."Crystal and molecular structure of DL-methionine nitrate," CAS 104:1975, 43 (1986).

Pradhan et al., Journal of Chemical and Engineering Data, 2000, 45(1):140-143.

Rajkumar and Ramakrishnan, "Infrared and Roman Spectra of L-Valine Nitrate and L-Leucine Nitrate", Journal of Raman Spectroscopy, 2000. p. 1107-1112, vol. 31. John Wiley & SonsLtd.

Jablecka et al.Med Sci Monit 10(I):CR29-32 (2004).

Maynard et al., "High Levels of Dietary Carnosine Are Associated with Increased Concentrations of Carnosine and Histidine in Rat Soleus Muscle," J. Nut. 131:287-290 (2001).

Rytlewski et al.European Journal of Obstetrics & Gynecology and Reproductive Biology 138:23-28 (2008).

Schwedhelm et al., "Pharmacokinetic and pharmacodynamics properties of oral L-citrulline and L-arginine: impact on nitric oxide metabolism," Br J Clin Pharmacol 65(1):51-59 (2007).

Smith et al."Nitric oxide precursors and congenital heart surgery: A randomized controlled trial of oral citrulline," J Thorac Cardioasc Surg 132:58-65 (2006).

Rytlewski et al., Effects of prolonged oral supplementation with L-arginine on blood pressure and nitric oxide synthesis in preeclampsia, Eur J Clin Lnvest 35(1):32-37 (2005).

Ming et al.Circulation 110:3708-3714 (2004).

Romero et al., "Therapeutic Use of Citrulline in Cardiovascular Disease," Cardiovascular Drug Reviews 24(3-4):275-290 (2006).

Oka et al.Vasc Med 10:265-274 (2005).

Hayashi et al.PNAS 102(38):13681-13686 (2005).

Grasemann et al., "Oral L-arginine supplementation in cystic fibrosis patients: a placebo-controlled study," Eur Respir J 25:62-68 (2005).

Boger, "The Pharmacodynamics of L-Arginine," J. Nutr. 137:1650S-1655S (2007).

Berge et al., Journal of Pharmaceutical Science, 66(1):1-19, 1977.

Takahashi et al."Characterization of the influence of nitric oxide donors on intestinal absorption of macromolecules," International Journal of Pharmaceutics 286:89-97 (2004).

Fetih et al."Nitric oxide donors can enhance the intestinal transport and absorption of insulin and [Asu1,7]-eel calcitonin in rats," Journal of Controlled Release 106:287-297 (2005).

Fetih et al."Excellent Absorption Enhancing Characteristics of NO Donors for Improving the Intestinal Absorption of Poorly Absorbable Compound Compared with Conventional Absorption Enhancers," Drug Metab. Pharmacokinet. vol. 21(3):222-229 (2006).

Aniya et al., "Evaluation of Nitric Oxide Formation from Nitrates in Pig Coronary Arteries," Jpn. J. Pharmacol. 71:101-107 (1996).

Luscher, "Endogenous and exogenous nitrates and their role in myocardial ischaemia," Br. J. Clin. Pharmacol. 34:29S-35S (1992).

Shiraki et al., "The hypotensive mechanisms of the new anti-anginal drugN-(2-Hydroxyethyl) Nicotinamide Nitrate (SG-75) in beagle dogs," Japan. J. Pharmacol. vol. 31:921-929 (1981).

Slart et al., "Nitrate Administration Increases Blood Flow in Dysfunctional but Viable Myocardium, Leading to Improved Assessment of Myocardial Viability: A PET Study," J Nucl Med 47:1307-1311 (2006).

Fayers et al."Nitrate tolerance and the links with endothelial dysfunction and oxidative stress," Br J Clin Pharmacol 56:620-628 (2003).

Harm J. Knot. "Nitrate Tolerance in Hypertension New Insight Into a Century-Old Problem," Circulation Research vol. 93:799-801 (2003).

Schulz et al., "Functional and Biochemical Analysis of Endothelial (Dys)function and NO/cGMP Signaling in Human Blood Vessels with and without Nitroglycerin Pretreatment," Circulation 105:1170-1175 (2002).

Hatanaka et al."Stereoselective Pharmacokinetics and Pharmacodynamics of Organic Nitrates in Rats," J Pharmacol Exp Ther. vol. 298(1):346-53 (2001).

Chabot et al., "Characterization of the vasodilator properties of peroxynitrite on rat pulmonary artery: role of poly (adenosine 5'-diphosphoribose synthase," British Journal of Pharmacology 121:485-490 (1997).

Bauer et al., "Vascular and Hemodynamic Differences between Organic Nitrates and Nitrites," Journal of Pharmacology and Experimental Therapeutics 280:326-331 (1997).

Niu et al."Vasorelaxant effect of taurine is diminished by tetraethylammonium in rat isolated arteries," European Journal of Pharmacology 580:169-174 (2008).

Tan et al., "Taurine protects against low-density lipoprotein-induced endothelial dysfunction by the DDAH/ADMA pathway," Vascular Pharmacology 46:338-345 (2007).

Ahtee et al."Taurine Biological Actions and Clinical Perspectives," J. Nutr. 116:2555-2556 (1986).

Larsen, Effects of dietary nitrates on oxygen cost during Exercise, B. Acta Physiol 191(1 ):59-66 (2007).

Bloomer et al."Glycine propionyl-L-carnitine increases plasma nitrate/nitrite in resistance trained men," Journal of the International Society of Sports Nutrition 4(22):1-6 (2007).

Ramaswamy et al."Vibrational spectroscopic studies of L-argininium dinitrate," J. Raman Spectrosc. 34:50-56 (2003).

(56) References Cited

OTHER PUBLICATIONS

Petrosyan et al., J. Molecular Structure, 794: 160-167, 2006.
Beghetti et al. "Nitric oxide precursors and congenital cardiac surgery: A randomized controlled trial of oral citrulline. Definition of pulmonary hypertension in Fontan circulation?" J Thorac Cardioasc Surg 132(6):1501-1502 (2006).
CFIndustries, "Material Safety Data Sheet for Urea Ammonium Nitrate Solution (UAN)," available at www.cfindustries.com/pdf/UANMSDS.pdf Oct. 25, 2006.
Glyceryl trinitrate—leaflet print—Patient UK, available at http://www.patient.co.uk/printer.asp?dock=30003883, 2009.
Xu et al., "Composite medical preparation for promoting hair growth," CAS: 143:103285 (2005).
B. Sridhar, et al, "Bis (beta-alanine) Hydrogen Nitrate", Acta Crystallographica Section, 2001, pp. 1004-1006vol. 57.
Bauer et al. "Photochemical Generation of Nitric Oxide from Nitro-containing Compounds: Possible Relation to Vascular Photorelaxation Phenomena," Life Science 54(1):PL1-PL4 (1994).
Sridhar et al., "L-Aspartic Acid Nitrate-L-Aspartic Acid," Acta Cryst. E58:o1372-o1374 (2002).
Rao et al. "Structure and Conformational Aspects of the Nitrates of Amino Acids and Peptides. I. Crystal Structure of Glycylglycine Nitrate," Acta Cryst. B29:2379-2388 (1973).
Chang et al., "Arginase modulates nitrix oxide production in activated macrophages," Am. J. Physiol., 274: H342-348, 1998.
Magg, G.W., Hecker, R.J. and Whitaker, P.A., "Nitrogenous Compounds in Sugarbeet Juices", Journal of the American Society of Sugar Beet Technologists, 1972; vol. 17, No. 2pp. 154-164.
Material Safety Data Sheet—L-Arginine.
Material Safety Data Sheet—B-Alanine MSDS.
Material Safety Data Sheet—L-Glutamine MSDS.
Material Safety Data Sheet—L-leucine MSDS.
Material Safety Data Sheet—L-Norvaline.
Amidon, G. L. et al., "Intestinal Absoption of Amino Acid Derivatives: Structural Requirements for Membrane Hydrolysis.", Journal of Pharmaceutical Sciences., (1983), vol. 72, No. 8, pp. 943-944, XP055127041.
Anders et al. "Aminoacylases", 1994, Advances in Pharmacology, vol. 27, pp. 431-448. (Year: 1994).
Artioli et al. "Role of beta-Alanine Supplementation on Muscle Carnosine and Exercise Performance" Med. Sci. Sprots Exerc, Jun. 2010, vol. 42, No. 6pp. 1162-1173.
Blodgett et al. "Incidence of Hematologic Disease in Patients with Carpal Tunnel Syndrome" JAMA, 1962, 182(7), pp. 814-815.
Harris et al. "The absorption of orally supplied beta-alanine and its effect on muscle carnosine synthesis in human vastus lateralis" Amino Acids, 2006, vol. 30, pp. 270-289. (Year: 2006).
Sale et al. Effect of beta-alanine supplementation on muscle carnosine concentrations and exercise performance. Amino Acids, 39:321-333, 2010.
Simplico et al. "Prodrus for Amines", Molecules 2008, vol. 13, pp. 519-547.
Urakami, M. et al., "Relationship between Structure and Permeability of Tryptophan Derivatives Across Human Intestinal Epithelial (Caco-2) Cells.", Z. Naturforsch., (2003), vol. 58C, pp. 135-142, XP055127040.
Wilson et al., "Beta-Alanine-Bad Ass Supplement", Iron Man Magazine, Oct. 13, 2010.
Sastre et al. "Metabolism of agmatine in macrophages: modulation by lipopolysaccharide and inhibitory cytokines," Biochem. J. 330:1405-1409 (1998).
Basheva et al. "Role of Betaine as Foam Booster in the Presence of Silicone Oil Drops," Langmuir 16:1000-1013 (2000).
Ilczyszyn et al. CAS: 145:83630 2006.
Piccolo et al. CAS: 138: 1375892003.
Flaherty, 1989, Drugs, 137:523-550.
Elmore et al., "Compilation of free amino acid data for various food raw materials, showing the relative contributions of asparagine, glutamine, aspartic acid and glutamic acid to the fee amino acid composition", Oct. 2002, JIFSAN Acrylamide in Food Workshop, Chicago. (Year 2002).
Stephany et al. "The Intake of Nitrate, Nitrite and Volitile N-Nitrosamins and the Occurrence of Volatile N-nitrosamines in human urine and Veal Calves" IARC Scientific Publications, Jan. 1978, vol. 19, pp. 443-460. (Year: 1978).
Lewis et al. Publication, Pharmacol. Biochem Behav, 2007, 88(1): 114-21.
Thandani, U. "Challenges with Nitrate Therpy and Nitrate Tolerance: Prevalence , Prevention, and Clinical Relevance" Am J Cardiovasc Drugs, 2014, vol. 14, pp. 287-301. (Year: 2014).
Kou et al. Applicaiton No. 200410009958.3, 2005.
S. Ramaswamy, Acta Cryst., E58, 646-648 (2002).
Dhas, S.A. Martin Britto et al., Growth and Characterization of a New Organic NLO Material; Glycine Nitrate, ScienceDirect, Optics communications 278 (2007) 434-438.
Santamaria et al. "A survey of nitrate and oxalate content in fresh vegetables" Journal of the Science of Food and Agriculture, 1999, vol. 79, 1882-1888. (Year: 1999).
Gibson et al. "Protective role of the epithelium of the small intestine and colon", inflamm. Bowel Dis., 1996, vol. 2, No. 4, pp. 279-302, abstract provided. (Year: 1996).
Kemmerer et al. Publication, J. Nutr., 1949, 38(4): 527-33.
Gao et al., Life Science, 1995, 57: 83-86.
Sen et al. Journal of Association of Official Analytical Chemists, 61(6): 1389-1394, 1978.
Atanasova, Plant Siol Environ, 2008, 54(2):66-71.
Hui or Shi et al., Handbook of Food Science, Technology, and Engineering, 2006, vol. 4, Chapter 170, p. 170-1-170-9.
The product L-Leucine nitrate power by Body Ripped, for sale, 2014.
The product valine nitrate power with a Brand name Hobid, for sale, 2014.
The product Isoleucine nitrate power with a Brand name Hobid, for sale, 2014.
The product APS Creatine Nitrate , for sale, 2014.
The product L-glutamine nitrate power with a Brand name Hobid, for sale, 2014.
San Corporation dietary supplement containing creatine nitrate, 2006.
MrSupplement.com product dietary supplement Creatine Nitrate, 2006.
Betancourt product: Betancourt Ripped Juice EX2, 2006.
Henriksson et al., Acta Physiol, Sep. 1, 2007, 191:1.
IForce Nutrition product "Potassium Nitrate", 2006.
Luigi et al., Med. Sc.i Sports Exerc., 1999, 31(12): 1748-54.
Zhang et al. Publication, Amino acids, 2004, 26:203-207.
Dessaignes et al., The Chemist or Chemical & Physical Science, 1854, pp. 594-597.
Ignarro et al. Publication, The Journal of Pharmacology and Experimental Therapeutics, 1988, 244(1): 181-189.
Feelisch et al., Eur J. Pharmacol., 1987, 139(1):19-30.
Walker et al., Food additive and Contaminants, 1990, 7(6):717-768.
Creatine from Wikipedia, 2017.
Creatine nitrate from PubChem, 2017.
Kenechuwu et al. J. Microencapsul, 2017, 34(6):592-609.
Honikel's publication, Meat Science, 2008,78: 68-76.
BSN Volumaize Aretic Blast, on line, sale product, 2014.
PS Nutrition Creatine Nitrate, on line, sale producr, 2014.
Giant Sport Metabolic Bioshock—Workout Supplement, on line, sale product, 2014.
Sader et al., "Endothelial Function, Vascular Reactivity and Gender Differences in the Cardiovascular System", Cardiovascular Research 53 (2002) 597-604, Aug. 21, 2001.
Stout et al., "Effects of B-Alanine Supplementation on the onset of Neuromuscular Fatigue and Ventilatory Threshold in Women", Amino Acids (2006), Springer-Verlag 2006.
Dymatize Nutrition, "Xpand 2x 10 Serving—Dymatize Nutritional Supplements, Whey Protein, Bodybuilding", http://www.dymatize.com/store/p/289-Xpand-2x-10-Servings.html—Advertisement. 2014.
Dymatize Nutrition, "Pre-Workout", http://www.dymatize.com/nitric-oxide, Mar. 31, 2014—Advertisement.

(56) References Cited

OTHER PUBLICATIONS

Chemical Abstracts Service, "Chemical Abstracts", The American Chemical Society, Liquid Crystals, vol. 104, Jun. 2, 1986.
GNC Mega Men, "GNC Mega Men 90 Caplets", http://www.gnc.com/GNC-Mega-Men-reg/product.jsp?productId=4033432, Apr. 22, 2014.
ProArgi 9 Supplement Website: ProArgi-9 Plus FAQ, "ProArgi 9 Plus Site", http://proargi9site.blogspot.com/p/proargi-9-plus-faq.html, Apr. 22, 2014.
Summary of Studies of B-Alanine and sports performance, "Studies of B-Alanine Supplementation on Exercise Capacity or Performance", Nov. 2011.
Watts, "A Dictionary of Chemistry and the Allied Branches of Other Sciences", Library of the University of California, Aug. 1808.
Watt et al., "The Chemist, A Monthly Journal of Chemical & Physical Science", vol. 1, London; Samuel Highley, 32 Fleet Street, 1854.
Weitzberg et al., "Dietary Nitrate—A Slow Train Coming", J Physiol 589.22 (2011) pp. 5333-5553, 2011 The Authors. Journal compilation, 2011 The Physiological Society.
Zhu et al., "Expression of Human Arginine Decarboxylase, the Biosynthetic Enzyme for Agmatine", NIH Public Access, Biochim Biophys Acta. Jan. 22, 2004; 1670(2): 156-164.
Ziegenfuss et al., "Effect of a Supplement Containing Primarily Beta Alanine, Arginine, Creatine Malate, and Glycerol Monostearate on Exercise-Induced Changes in Lean Mass of the Arms", Journal of the International Society of Sports Nutrition 2008, 5(Suppl 1):p. 16 doi:10.1186/1550-2783-5-S1-P16.
"Dymatize Nutritional Supplements, Whey Protein, Bodybuilding & Weight Products", 2013 Dymatize Enterprises LLC, Xpand 2x 36 Serving, http://www.dymatize.com/products/nitric-oxide/detail/1166/xpand-2x-36-serving, 2013.
Abou-Mohamed et al. "Role of L-Arginine in the Vascular Actions and Development of Tolerance to Nitroglycerin", British Journal of Pharmacology (2000) 130, 211-218.
"Xpand 2x by Dymatize at Bodybuilding.com—Lowest Price on Xpand 2x!", Advertisement, 2012 BodyBuilding.com, LLC., http://www.bodybuilding.com/store/dymatize/xpand-2x.html, Jun. 8, 2013.
Dymatize® Xpand 2x®, Fruit Punch, Dymatize—GNC, www.gnc.com/product/index.jsp?productId=13180805, Jun. 17, 2013, p. 1-2.
Bloomer et al., "Comparison of pre-workout nitric oxide stimulating dietary supplements on skeletal muscle oxygen saturation, blood nitrate/nitrite, lipid peroxidation, and upper body exercise performance in resistance trained men", Journal of the International Society of Sports Nutrition 2010, 7:16, http://www.jissn.com/content/7/1/16.
Bover-Cid et al., "Biogeneic Amine Accumulation in Ripened Sausages Affected by the Addition of Sodium Sulphite", Meat Science 59 (2001) 391-396, Mar. 20, 2001.
Del Compo et al., "Creatinine, creatine and protein in cooked meat products", Food Chemistry, vol. 63, No. 2, pp. 187Y190, 1998.
Eaton et al., "Urinary Beta-Alanine Excretion is a Marker of Abnormal as well as Normal Gut Fermentation", Journal of Nutritional & Environmental Medicine (Jun. 2004) 14(2), 121-127.
Hoffman et al., "Effect of Creatine and β-Alanine Supplementation on Performance and Endocrine Responses in Strength/Power Athletes", International Journal of Sport Nutrition and Exercise Metabolism, 2006, 16, 430-446, © 2006 Human Kinetics, Inc.—20.
Hunter et al., "The Inhibition of Arginase By Amino Acids", Department of Pathological Chemistry, University of Toronto, Canada, Jul. 24, 1944.
Ignarro et al., "Pharmacology of Endothelium-derived Nitric Oxide and Nitrovasodilators", The Western Journal of Medicine, Jan. 1991, 154.
Jamalian et al., "Nutritional Value of Middle Eastern Foodstuffs", Jamalian & Pellett : Nutritional Value of Middle Eastern Foodstuffs. IV, Dec. 1967.
Kendrick et al., "The effect of 4 weeks B-alanine supplementation and isokinetic training on carnosine concentrations in type I and II human skeletal muscle fibres", Eur J Appl Physiol (2009) 106:131-138, Feb. 12, 2009.
Kernohan et al., "An oral yohimbine/L-arginine combination (NMI 861) for the treatment of male erectile dysfunction: a pharmacokinetic, pharmacodynamic and interaction study with intravenous nitroglycerine in healthy male subjects", British Journal of Clinical Pharmacology, © 2004 Blackwell Publishing Ltd.
Lundberg et al., "Cardioprotective effects of vegetables: Is nitrate the answer?", Science Direct, Jan. 2006.
Lundberg et al., "The nitrate-nitrite-nitric oxide pathway in physiology and therapeutics", 2008 Nature Publishing Group, Feb. 2008, vol. 7.
Riens et al., "Amino Acid and Sucrose Content Determined in the Cytosolic, Chloroplastic, and Vacuolar Compartments and in the Phloem Sap of Spinach Leaves1", Plant Physiol. (1991) 97, 227-233, Apr. 6, 1991.
Rimando et al., "Determination of Citrulline in Watermelon Rind", Journal of Chromatography A, 1078 (2005) 196-200, May 2, 2005.
Avraham et al., "Tyrosine improves appetite cognition and exercise tolerance in activity anorexia," Medicine & Science in Sports & Exercise, 33(12): 2104-2110, 2001.
Bendahan et al., "Citrulline/malate promotes aerobic energy production in human exercising muscle," Br. J. Sports Med., 36: 282-289, 2002.
Large Wendy, "Circuit training combines aerobic and anaerobic workouts into one," News Journal (Mansfield Ohio), Sep. 5, 2004.
Tannebaum et al., "Inhibition of nitrosamine formation by ascorbic acid," Am. J. Clin. Nutr. 53: 2475-2505, 1991.
Borison et al., "Brain 2-phenylethylamine as a major mediator for the central actions of amphetamine and methylphenidate," Life Sci., 17: 1331-1344, Nov. 1975.
Sugino et al., "L-ornithine supplementation attenuates physical fatigue in healthy volunteers by modulating lipid and amino acid metabolism," Nutrition Research, 2008, 28:738-743.
Barron JT and Parillo JE, "Production of lactic acid and energy metabolism in vascular smooth muscle: effect of dichloroacetate." Am J Physiol. Feb. 1995;268(2 Pt 2):H713-9.
Winter et al., "N-Nitrosamine Generation From Ingested Nitrate Via Nitric Oxide in Subjects With and Without Gastroesophageal Reflux," Gastroenterology, 2007, 133:164-174.
Del Pilar Garcia-Santos et al., "Reactivity of Amino Acids in Nitrosation Reactions and Its Relation to the Alkylating Potential of Their Products," J. Am. Chem. Soc., 2002, 124(10): 2177-2182.
Cavassa et al. WO98/43499.
Green et al. Publication, Sports Med., 1996, 21(2): 119-146.
Shen et al. Publication, Acta Physiol. Scand, 2000, 168(4): 675-86.
"Nitrates and Nitrites", TEACH Chemical Summary, U.S. EPA, Toxicity and Exposure Assessment for Children's Health, published by the U.S. Environmental Protection Agency on May 22, 2007 (Year: 2007).
21 C.F.R. (I)(B) §§ 172.160 and 172.170, revised Apr. 1, 2018 (Year: 2018).
Herbwisdom.com, 2006.
Amino Thrust dietary supplement, 2007.
PEScience High vol. 2007.
Arnold Iron CRE3, 2007.
"Dietary Nitrate and Nitrite to Increase Nitric Oxide in Patients with Coronary Artery Disease," Clinical Trial available at http://clinicaltrials.gov/ct2/show/NCT00069654, 2010.
"Heart attack—Nitrates & vasodilators—Revolution health," available at http://www.revolutionhealth.com/conditions/heart/heart-attack/medication-types/nitrates-vasodilators, 2011.
"Nitrates and nitrites (PIM G016)," available at http://www.inchem.org/documents/pims/chemical/pimg016.htm, 2011.
Baran, "Crystal structure, phase transitions and vibrational spectra of bis(betaine) nitrate," Journal of Molecular Structure, 372: 131-144, 1995.
Wheatley et al., "Arginine deprivation and tumor cell death arginase and its inhibition," Molecular and Cellular Biochemistry, 244: 177-185, 2003.

(56) References Cited

OTHER PUBLICATIONS

Joy et al., "A multi-ingredient, preworkout supplement is apparently safe in healthy males and females," Food & Research, 59:27470, 2015.
http://www.curezone.org, no date given.
http://www.bodybuilding.com/store/fuel-one/6th-gear.html, no date given.
Bryan, N., "Food, Nutrition and the Nitric Oxide Pathway: Biochemistry and Bioactivity" 2010, pp. 59-63.
Schulbach et al., "Guide to nitrogen quick-tests for vegetables wit the 'cardy' nitrate meter" FREP Contract # 95/0582.
Muramoto, J., "Comparison of Nitrate Content in Leafy Vegetables from Organic and Conventional Farms in California" Center for Agroecology and Sustainable Food Systems University of California, Santa Cruz, 1999.
http://www.ergo-log.com/plaatjes/xpand2x.gif, no date given.
Anderson, K. "Nitrate and Nitrite in Human Nutrition" The Graduate College in the University of Nebraska, Lincoln, Nebraska, 1982.
ColorMaker, 2006.
http://www.beyondsupplements.com.au/index.php?route=product/, no date given.
http://www.dymatize.com/store/workoutsupport/M-P-ACT-Energy, no date given.
https://www.thesynergycompany.com/organic-carrot-juice-powder, no date given.
Rosen et al. "Nutrient Management for Commercial Fruit & Vegetable Crops in Minnesota" University of Minnesota extension Service, 2005 pp. 35-36 <https://conservancy.umn.edu/bitstream/handle/11299/51272/5886.pdf?sequence=1>.
RSPReGenBCAA, 2006.
BeetVO2Max—max Nitric Oxide Booster, Amazon.com, 2006.
NutraBioBCAA2500, 2006.
Arenas et al., Muscle & Nerve, 1991, 14:598-604.
Pariser et al. Cutis, 1994, 54(1): 43-44.
Huxtable et al. Physiological Reviews, 72(1):101-142, 1992.
Taurine from Nutrabio, 2006.
QuadraLean by RSP Nutrition, Bodybuilding.com, 2006.
Marconi, Int. J. Sports Med, 11 (1990):1-14.
Curtis, J., Dec. 6, 2017, "Nitrate-Free Bacon: Myth or Reality", https://firsthandfoods.com/author/jennifer/, pp. 1-2 (Year: 2017).
Fanous, S. "Is Sodium Nitrate Bad for You?", May 20, 2015, Healthline, https://www.healthline.com/health/food-nutrition/is-sodium-nitrate-bad-for-you#1, pp. 1-8. (Year: 2015).
Lundberg et al., Arterioscler. Thromb. Vasc. Biol., 25:915-922 (2005).
Harrison, D.G et al., "The Nitrovasodilators, new Ideas About Old Drugs," Circulation, vol. 87, No. 5, May 1993, pp. 1461-1467).
Stephenson, T., "How children's responses to drugs differe from adults," Br. J. Clin. Pharmacol., 59(6):670-673, 2005.
Stetson, C., "Characteristics of Adults vs. Children." [retrieved on May 4, 2016], Retrieved from the Internet <URL: http://www.ehow.com/info 8501147 characteristics-adults-vs-children.html>.
Fraser et al. Publication, circulation, 1983, 67(2): 405-412.
Ignarro ("After 130 years, the molecular mechanism of action of nitroglycerin is revealed," [online], Jun. 11, 2002 [retrieved on May 8, 2016] Retrieved from the Internet: <http://www.pnas.org/cgi/content/full/99/12/7816?ck=nck>).
Lonic Liquids ( URL: https://www.organic-chemistry.org/topics/ionic-liquids.shtm ), printed Apr. 2019 (Year: 2019).
English translation of KR-20110015141-A, Feb. 15, 2011, pp. 1-23 (Year: 2011).
Heart attack—Nitrates & vasodilators—Revolution Health, available at http://www.revolutionhealth.com/conditions/ heart/herat-attack/medication-types/nitrates-vasodilators/ 2011.
Examine.com, "L-Carnitine", Sep. 12, 2014, https://examine.com/supplements/l-carnitine/. (Year:2014).
Swensen et al. Publication, Intl. J. of Sports medicine, 1994, 15(7):430-4.
Material Safety Data Sheet—Taurine.

Boguslavskiy. Effect of nitric oxide on the efficiency of oxygen usage by a working skeletal muscle under fatigue, Fiziol. Zhum., vol. 51, No. 1, pp. 33-42 (2005) & Certified Translation.
Burtscher. The Proonged Intake of L-Arginine-L-Aspartate Reduces Blood Lactate Accumulation and Oxygen Consumption During Submaximal Exercise, Journal of Sports Science and Medicine, vol. 4, pp. 314-322 (2005).
C. Oldreive, et al., The Mechanisms for Nitration and Nitrotyrosine Formation in vitro and in vivo: Impact of D;et, Free Rad. Res., vol. 35, pp. 215-231 (2001).
Benjamin, Nigel, Nitrates in the Human Diet—good or bad?, Ann. Zootech. vol. 49, pp. 207-216 (2000).
G. Richardson, et al., The ingestion of inorganic nitrate increases gast,-; c S-nitrosothio/ levels and inhibits platelet unction in humans, Nitric Oxide, vol. 7, pp. 24-29 (2002).
F. Murad, Cyclic Guanosine Monophosphate as a Mediator of Vasodilation, J. Clin. Invest., vol. 78, pp. 1-5 (Jul. 1986).
J. Abrams, MD, Beneficial Actions of Nitrates in Cardiovascular Disease, The American Journal of Cardiology, vol. 77, pp. 31C-37C (May 30, 1996).
A Butler, et al., Medieval Chinese Medicine: The Dunhuang Medical Manuscripts (Chapter 16: A treatment for carenovascular dysfunction in a Dunhuang medical manuscript), Routledge (2005).
Pickering et al., Why Don't We Use Nitrates to Treat Older Hypertensive Patients?, Journal of Clinical Hypertension, vol. 7, No. 11, pp. 685-690 (Nov. 2005).
G.S. Stokes, et al., Long-Term Effectiveness of Extended-Release Nitrate for the treatment of Systolic Hypertension, Hypertension vol. 45, pp. 380-384 (2005).
G. M. McKnight, et al., Dietary nitrate in man: friend or foe?, British Journal of Nutrition, vol. 81, pp. 349-358 (1999).
B. C. Challis, Nutrition and nitrosamine formation, Proceeds of the Nutrition Society, vol. 44, pp. 95-100 (1985).
L. Brunton, et al., An Address on Longevity and the Means of Attaining It, The Lancet, vol. 168, Issue 4342, pp. 1330-1335 (Nov. 17, 1906).
G. M. McKnight, et al., Chemical synthesis of nitric oxide in the stomachfi-om dietary nitrate in humans, Gut, vol. 40, pp. 211-214 (1997).
K. Cosby, et al., Nitrite reduction to nitric oxide by deoxyhemoglobin vasodilates the human circulation, Nature Medicine, vol. 9, No. 12, pp. 1498-1505(Dec. 2003).
S. Moncada, et al., The L-Arginine:Nit ic Oxide Pathway, Journal of Cardiovascular Pharmacology, 17(Suppl. 3):S 1-S9 1991).
L. Appel, et al., A Clinical Trial of the Effects of Dietal J1 Patterns on Blood Pressure, N. Engl. J. Med., 336:16, pp. 1117-1124 (Apr. 17, 1997).
G. R. J. Thatcher, Serial Review: Mechanisms and Novel Directions in the Biological Applications of Nitric Oxide Donors, Free Radical Biology & Medicine, vol. 37, No. 8, pp. 1122-1143 (2004).
D. D. Rees, et al., Role of endothelium-derived nitric oxide in the regulation of blood pressure, Proc. Natl. Acad. Sci. USA, vol. 86, pp. 3375-3378 (May 1989).
K. Tsuchiya, et al., Malfunction of Vascular Control in Lifestyle-Related Diseases: Formation of Systemic Hemoglobin-Nitric Oxide Complex (HbNO) From Dietary Nitrite, J. Pharmacol Sci, vol. 96, pp. 395-400 (2004).
B. Spiegelhalder, et al., Influence of Dietary Nitrate On Nitrate Content of Human Saliva: Possible Relevance of N-Nitroso Compounds, Fd. Cosmet. Toxicol., vol. 14, pp. 545-548 (1976).
L. Brunton, An Address on Blood Pressure In Man: Its estimation and indications for treatment, The British Medical Journal, pp. 64-67 (Jul. 10, 1909).
Ximenes, M. I. N., et al., "Polarographic determination of nitrate in vegetables" Talanta 51 (2000) 49-56.
Shen, W., Nitric oxide production and NO synthase gene expression contribute to vascular regulation during exercise, Med. Sri Sports Fxerc., vol. 27, No. 8, pp. 1125 1134(Aug. I995).
Dhar et al., Complex Compounds of Acid, Base and Salt with Nitrogenous and Other Organic Substances, in National Academy of Sciences, India, Symposium on Nitrogen, Part 1, Section A, vol. 31, 1961, pp. 76-79.

(56) References Cited

OTHER PUBLICATIONS

Stryer, Lubert, Biochemistry, Third Edition, W.H. Freeman and Company, New York: 1988, pp. 16-23, 233-236, 500-502 and 934-936.
Rombauer, Irma S., "Joy of Cooking", 75th Anniversary, Scribner, New York, 2006, p. 163 (2006).
Declaration of Richard Chamberlin Under 37 C.F.R. § 1.132 dated Aug. 28, 2014.
"Isosorbide dinitrate—leaflet print—Patient UK," available at http://www.patient.co.uk/printer.asp?doc= 30003884, 2011.
"Isosorbide mononitrate-leaflet print—Patient UK," available at http://www.patient.co.uk/printer.asp?doc=30003885, 2008.
White, Handler and Smith, Principles of Biochemistry, Fifth Edition, McGrawy-Hill, New York:1973, pp. 89-95.
Mostad, A., Zeitschrift fur Kristallographie, 172: 175-182, 1985.
Cromwell et al., "The Biosynthesis and Metabolism of Betaines in Plants," 1953 Biochem J., 55: 189-192.
Danov et al., "Mixed Solutions of Anionic and Zwitterionic Surfactant (Betaine): Surface Tension Isotherms, Adsoprtion, and Relaxation Kinetics," 2004 Langmuir 20: 5445-5453.
Petersson et al., "Dietary nitrate increases gastric mucosal blood flow and mucosal defense," Am. J. Physiol. Gastrointest. Liver, 292: G718-G724, 2007.
Duncan et al., "Chemical generation of nitric oxide in the mouth from the enterosaliary circulation of dietary nitrate," Nature Medicine, 1 (6): 546-551, Jun. 1995.
Crooks et al., U. S. Patent Application Publication No. 2002/0065323 A1, published May 30, 2002.
Gao et al., "Agmatine: A Novel Endogenous Vasodilator Substance," Life Sciences, 57(8): 83-86, 1995.
Gwartney, D. L, "On the Horizon: Agmatine," Oct./Nov. 1998, Pump 101:96-97.
Kramer et al., U. S. Patent Application Publication No. 2009/076110 A1 published Mar. 19, 2009.
Parker et al., The Effect of Supplemental L-Arginine on Tolerance Development During Continuous Transdermal Nitroglycerin Therapy, J. of Am. Coll. of Cardiology, 39(7): 1199-1203, 2002.
Bahadur et al., "Crystal and molecular stucture of DL-aspartic acid nitrate monohydrate," Z. Kristallogr. 210: 276-278, 1995.
Declaration of Richard Chamberlin Dessaignes, Comptes Rendus 1854 Under 37 C.F.R. § 1.132 dated Aug. 15, 2014 filed in Reexam. Control Nos. 90/011,869 and 90/011,869.
Declaration of James L. Bono Under 37 C.F.R. § 1.132 dated Aug. 27, 2014.
Craig, "Betaine in human nutrition," Am J Clin Nutr, 80:539-549,2004.
Godzisz, "Classification and nature of hydrogen bonds to betaine. X-ray, 13C CP MAS and IR description of low barrier hydrogen bonds," Journal of Molecular Structure, 606:123-137,2002.
Haussuhl, "Elastic and thermoelastic properties of twelve adducts of betaine," Z Kristallogr, 188:311-320,1989.
Miller, Elements of Chemistry—Theoretical and Practical, Longsmans, Green, Reader and Dyer, 1969, pp. 757-770.
Rajkumar et al., "Infrared and Raman spectra of DL-aspartic acid nitrate monohydrate," Spectrochimica Acta Part A, 54:1527-1532, 1998.
Srinivasan et al., "L-phenylalanine-nitric acid (2/1)," Acta Crystallographica E57:o916-o918, 2000.
Di Pasquale MG. Amino Acid and Proteins for the Athelete: The Anabolic Edge. CRC Press LLC, 1997, pp. 99-145.
Eppendorfer et al., "Free and Total Amino Acid Composition for Edible Pears, Beans, Kale, Spinach, Cauliflower, and Potatoes as Influenced by Nitrogen Fertilisation and Phosphorus Deficiency," J.Sci. Food Agric. 71 449-458, 1996.
Ilczyszyn et al. 13C chemical shift tensors of hydrogen bonded amino acids: Relations between experimental and calculated results. Chemical Physics 323 (2006) 231-242.
R.C. Harris et al., "The Influence of Beta-Alanine Supplementation and Training on the Muscle Carnosine Content in Human v. Iateralis, and the Effect of This on Exercise Performance," Amino Acids 29:12-13 (2005).
https://nuts.com/cookingbaking/powders/beet.html, 2016.
Vytech advertisement for "Nitrobol Extreme" Joe Welder's Muscle & Fitness, Sep. 2005.
EAS advertisement for "Phosphagen Elite" Joe Welder's Muscle & Fitness, Sep. 2005.
Optimum Nutrition advertisement for "Adenergy Stack" Joe Weider's Muscle & Fitness, Sep. 2005.
Nature's Best advertisement for "Perfect L-Glutamine" Joe Weider's Muscle & Fitness, Sep. 2005.
U.S. Food & Drug Administration document with respect to 21 CFR §184.1878 for thiamine mononitrate (Year: 2018).
Merriam-Webster definition of supplement https://www.merriam-webster.com/dictionary/supplementlaccessed Jun. 20, 2019] (Year: 2019).
Ruel et al., "Modulation in Angiogenic Therapy randomized controlled trial," J Thorac Cardiovasc Surg 135:762-770 (2008).
Eto et al. Publication, Archives of Physiology and Biochemistry, 1995, 103(2):160-4.
Vandenberghe et al. publication, J. Appl physiol, 1997, 83:2055-2063.
Larsen et al. Publication, New England Journal of Medicine, 2006, 2792-2793.
Barger, G. (1914) The Simpler Natural Bases. In R.H.A. Plimmer & F.G. Hopkins (Eds.) Monographs on Biochemistry (pp. 157-163) Longmans, Green & Co., London.
Beverly International advertisement in Dec. 1987 edition of Muscle & Fitness.
Lundberg et al., Inorganic nitrate is a possible source of systemic generation of nitric oxide, Free Radical Biology Medicine, vol. 37, No. 3. pp. 395-400, 2004.
Archer, Evidence that ingested nitrate and nitrite are beneficial to health, Journal of food protection, vol. 65, No. 5, pp. 872-875, 2002.
Pischel et al. CAS: 134:71896, 2001.
Schaefer et al., Intl. J. of Sports Medicine, 2002, 23(6):403-407.
Tao, Guo-Hong et al., New Generation Ionic Liquids: Cations Derived From Amino Acids, The Royal Society of Chemistry, ChemComm, Jun. 9, 2005, 3562-3564.
Elkayam et al. "Prevention of nitrate tolerance with concomitant administration of hydralazine" Can J CArdiol, 1996, vol. 12, suppl C, pp. 17C-21C. (Year: 1996).
Edwards et al., "Amino Acids in Foods, Cystine, Tyrosine, and Essential Amino Acid Contents of Selected Foods", Agricultural and Food Chemistry, vol. 3, No. 11 , Nov. 1955.
Hord et al., "Food sources of nitrates and nitrites: the physiologic context for potential health benefits1-3", Perspective, Am J Clin Nutr 2009;90:1-10, American Society for Nutrition.
Bailey et al. "Dietary nitrate supplementation reduces the O2 cost of low-intensity exercise and enhances tolerance to high-intensity exercise in humans", J. Appl. Physiol., 2009, vol. 107, pp. 1144-1155. (Year: 2009).
Terzyan et al., "L-Arginine Nitrates," Journal of Molecular Structure 687:111-117 (2004).
Ishii et al., "High glucose augments arginase activity and nitric oxide production in the renal cortex," Metabolism 53(7):868-874 (2004).
Abd El-Gawad et al. AAPS PharmaSciTech, 2017, 18(5):1795-1809.
CAS Registry No. 89695-59-0 (1984).
Material Safety Data Sheet—Agmatine sulfate salt.
L. Stryer, Biochemistry, Third Edition, W. H. Freeman and Company, pp. 15-24, 261-268, 499-502, and 933-936, New York, 1988.
FDA Regulation 42 FR, 1977.
USDA and HHS Agencies Work Together to Examine the Jurisdiction of Certain Food Categories, USDA & FDA, 2005.
CPG Sec 565.100 FDA Jurisdiction Over Meat and Poultry Products, 2005.
USDA Regulation 64 FR 72168, Food Ingredients and Sources of radiation Listed or Approved for Use in the Production of Meat and Poultry, 1999.

(56) References Cited

OTHER PUBLICATIONS

F. Ray, Meat Curing, ANSI-3994, OSU.

FDA Regulation 48 FR 1701, Indirect Food Additives; Paper and Paperboard Components, FDA, 1983.

L. Noah et al, Starting from Scratch?: Reinventing the Food Additive Approval process, Boston Univ. L. Rev. vol. 78:329, pp. 329-443 1998.

Ingested Nitrate and Nitrite, and Cyanobacterial Peptide Toxins, World Health Organization International Agency for Research on Cancer (2010).

Ashenhurst ([online] retrieved on Aug. 18, 2023 from: https://www.masterorganicchemistry.com/2018/02/28/amides-properties-synthesis-and-nomenclature/ 3 pages) (Year: 2023).

Carbonyl diamine [online] retrieved on Aug. 18, 2023 from: https://www.chembk.com/en/chem/Carbonyl%20diamine;1 page. (Year: 2023).

B. Pejin et al., Heavy metal content of a medicinal moss tea for hypertension, Natural Product Research, Taylor & Francis, 2012 vol. 26, No. 23, 2239 2242.

B. Pejin et al., Mineral Content of a Moss Tea for Hypertention, Italian Journal of Food Science, Italy Codon Publications, 2013 vol. 25, 235 237.

Vilskersts. R. et al. Magnesium nitrate attenuates blood pressure rise in SHR rats. Magnes Res. Jan.-Mar. 2014; 27(1): 16-24. doi:10.1684/mrh.2014.0358. PMID: 24827813.

Zhang et al. Effects of Magnesium Supplementation on Blood Pressure: A Meta-Analysis of Randomized Double-Blind Placebo-Controlled Trials. Hypertension. Aug. 2016;68(2):324-33. doi: 10.1161/HYPERTENSIONAHA.116.07664. Epub Jul. 11, 2016. PMID: 27402922.

Galachiev S.M. et al: Possibilities of endogenous formation of nitrosamines in gastric juice In Vitro, Samara Scientific Center of the Russian Academy of Sciences Bulletin, 2011, vol. 13, No. 1(7), pp. 1678-1680.

Kumar et al., "Chemical Denitrificaiton of Water by Zero-Valent Magnesium Powder." Journal of Hazardous Materials B135 (2006) 112-121). (Year: 2006).

Magnesium, Britannica Online Encyclopedia [online] retrieved on May 30, 2024 from: https://www.britannica.com/print/article/356899; 3 pages.) (Year: 2024).

Raymond et al., "Effects of Acute Red Spinach Extract Ingestion on Repeated Sprint Performance in Division I NCAA Female Soccer Athletes." (Oxygen 2023;3:133-142). (Year: 2023).

\* cited by examiner

METHODS OF INCREASING BLOOD OXYGEN SATURATION

CROSS-REFERENCE TO RELATED APPLICATIONS

The present application claims priority to U.S. Provisional Patent Application No. 63/113,114, filed Nov. 12, 2020; U.S. Provisional Patent Application No. 63/148,517, filed Feb. 11, 2021; and U.S. Provisional Patent Application No. 63/232,852, filed Aug. 13, 2021, the contents of each of which are hereby incorporated by reference in their entireties.

TECHNICAL FIELD

The present invention relates generally to compositions for oral administration and related methods of use for the effective and safe treatment of patients suffering from abnormally low SpO2 levels (e.g., <95%), caused by either respiratory infection, such as a Covid-19 infection, or other causes.

BACKGROUND

Acute respiratory distress syndrome (ARDS) occurs when lungs are severed injured, which can be from an infection or trauma. At the onset of ARDS, fluid from the smallest blood vessels in the lungs starts to leak into the alveoli, which causes the lungs to become smaller and stiffer. Patients find it harder to breath, and the amount of oxygen in the blood falls. Once the body is starved of oxygen (hypoxemia), damage to the brain and other tissues leads to organ failure. ARDS patients need help to open closed airspaces, get oxygen into the blood and make it easier to breath. A ventilator and extra oxygen are used for these reasons and maintained until the injury resolves.

Up to 25% of ARDS survivors develop physiologic evidence of restrictive lung disease within six months of ARDS diagnosis. More severe, prolonged illness and pulmonary causes of ARDS are thought to be risk factors for progression to fibrosis. Fibrotic lung disease can be a complication of prolonged respiratory failure from ARDS. Abnormalities on pulmonary function testing in ARDS survivors usually resolve with time. However, up to 25% of patients have persistent restrictive abnormalities six months after ARDS diagnosis, and many also have residual imaging abnormalities. These findings can be consistent with fibrosis. In fact, more severe, prolonged illness and pulmonary causes of ARDS are thought to be risk factors for progression to fibrosis.

Coronavirus disease 2019 (COVID-19) is a contagious respiratory and vascular disease. Specifically, it is a severe acute respiratory syndrome caused by the novel coronavirus SARS-CoV-2. Common symptoms include fever, cough, fatigue, shortness of breath or breathing difficulties, chest pain and loss of smell and taste. Another common symptom of COVID-19 is low blood oxygen saturation, with many patients showing oxygen saturation levels of lower than the normal 95%-100% range. Critically ill patients show oxygen saturation levels below 50% and death can come from low oxygenation through the lungs.

While most people have mild symptoms with COVID-19, some people develop ARDS, possibly precipitated by cytokine storm, multi-organ failure, septic shock, and blood clots. COVID-19 patients that develop ARDS are typically diagnosed by measuring their blood oxygen saturation (SpO2) levels, which are typically below the normal levels of 95% to 100%. In hospital environments, a patient's arterial oxygen saturation (SaO2) can also be measured, which directly measures the amount of oxygen gas in a patient's blood from a blood sample. Normal levels of SaO2 are also typically 95% to 100%. A medical professional could utilize both SpO2 and SaO2 to determine if a subject suffers from hypoxia. Longer-term damage to organs (in particular, the lungs and heart) has been observed, and there is concern about a significant number of patients who have recovered from the acute phase of the disease but continue to experience a range of effects (including severe fatigue, memory loss and other cognitive issues, low grade fever, muscle weakness, breathlessness, and other symptoms) for months afterwards. A lot of COVID-19 patients that develop ARDS survive their SARS-CoV-2 infection, but many of them have long lasting lung damage with persistent symptoms such as fatigue, tiredness, inability to exercise, inability to work, inability to perform sexual activity, burnout, collapse, exhaustion, frazzle, lassitude, prostration, weariness or fatigue, worsening of symptoms after physical or mental activities (also known as post-exertional malaise), difficulty thinking or concentrating (sometimes referred to as "brain fog"), cough, chest or stomach pain, headache, fast-beating or pounding heart (also described as heart palpitations), joint pain, muscle pain, sensation of pins-and-needles (paresthesia), diarrhea, sleep problems, fever, dizziness on standing (lightheadedness), rash, mood changes, changes in sense of smell or taste (anosmia), and changes in menstrual period cycles. These symptoms can persist for months afterwards a SARS-CoV-2 infection.

Some people who had severe illness with COVID-19 experience multiorgan effects or autoimmune conditions over a longer time with symptoms lasting weeks or months after COVID-19 illness. Multiorgan effects can affect many, if not all, body systems, including heart, lung, kidney, skin, and brain functions. Autoimmune conditions happen when your immune system attacks healthy cells in your body by mistake, causing inflammation (swelling) or tissue damage in the affected parts of the body.

While rare, some people (mostly children) develop multisystem inflammatory syndrome (MIS) during or immediately after a SARS-CoV-2 infection. MIS is a condition where different body parts can become inflamed. MIS can lead to post-COVID conditions if a person continues to experience multiorgan effects or other symptoms. These symptoms and diagnosis can remain for months.

Past epidemics caused by coronaviruses are instructive in that 30% of SARS and MERS survivors had persistent radiographic abnormalities and 15% had persistent physiologic restriction in their lungs. Risk factors for fibrosis were older age and ICU admission. Studies from China have reported persistent radiographic findings and abnormal lung function in COVID-19 survivors at discharge. Pre-COVID-19 research suggests post-ARDS fibrosis does not progress. Patients with post-ARDS fibrosis demonstrate stable impairment in pulmonary function, not the progression seen in interstitial lung diseases such as idiopathic pulmonary fibrosis (IPF). Similarly, no study of post-ARDS fibrosis has reported acute exacerbations like those seen in IPF. Proposals are emerging to study antifibrotics in COVID-19 ARDS.

So far, no solution exists for the successful management, treatment, or cure of COVID-19 patients suffering from long lasting lung damage. With new COVID-19 variants that show resistance or immunity to vaccination developing and the dominant spreading variant spreading to more regions, the need for a prevention, treatment, cure medication or supplementation formulation has been greater than ever.

Respiratory distress, leading to lower than normal oxygen saturation (i.e., SpO2 of less than 95%) can also happen in people with asthma during a severe attack, which can be deadly. Asthma causes swelling of the airways. This results in narrowing of the airways that carry air from the nose and mouth to the lungs. Allergens or irritating things entering the lungs trigger asthma symptoms. Symptoms of an asthma attack include trouble breathing, wheezing, coughing, and tightness in the chest.

Today, more Americans than ever are diagnosed with asthma—approximately 25 million Americans in 2020. This equals to about 1 in 13 Americans, including 8 percent of adults and 7 percent of children. About 20 million U.S. adults ages 18 and over have asthma. In adults, asthma is more common in women than men. Asthma is also the leading chronic disease in children. As of 2020, there are about 5.1 million children under the age of 18 with asthma. In children, asthma is more common in boys than girls. In 2019, 44.3% of children ages 18 and younger who had asthma reported having one or more asthma attacks in the past year. About 47.2 percent of children under the age of 5 with asthma had an episode. Among children ages 5 to 17, asthma is one of the top causes of missed school days. In 2013, it accounted for more than 13.8 million missed school days.

On average, ten Americans die from asthma each day. In 2019, 3,524 people died from asthma. Many of these deaths are avoidable with proper treatment and care. Adults are five times more likely to die from asthma than children. Women are more likely to die from asthma than men, and boys are more likely than girls.

Racial and ethnicity also affect the physical and socioeconomic outcomes of related to asthma. In fact, asthma frequency, illness, and death are highly connected with poverty, city air quality, indoor allergens, not enough patient education, and poor health care. The rate of asthma and the prevalence of asthma episodes is highest among Black Americans. Black Americans are five times more likely than white Americans to visit the emergency department due to asthma. Black Americans are also nearly three times more likely to die from asthma than white Americans. Among children, Black children are three times as likely to have asthma compared to white children. When sex is factored in, Black females have the highest rate of fatality due to asthma. In 2019, Black women were three times more likely to die from asthma than white men.

Asthma is one of this country's most common and costly diseases. In 2016, asthma accounted for 9.8 million doctor's office visits. In 2018, asthma accounted for 178,530 discharges from hospital inpatient care and 1.6 million emergency department visits. From 2008-2013, the annual economic cost of asthma was more than $81.9 billion—including medical costs and loss of work and school days: >$3 billion in losses due to missed work and school days; >$29 billion due to asthma-related mortality; and >$50.3 billion in medical costs. The annual per-person incremental medical cost of asthma was $3,266 (in 2015 U.S. dollars).

While asthma can be managed with proper prevention and an attack can be treated with a bronchodilator inhaler, there is no cure for asthma. Unfortunately, inhalers do not resolve the chest discomfort associated with asthma, and both steroid and bronchodilator inhalers have a number of side effects. Other disadvantages of using inhalers to manage asthma include lack of availability, the need for many doses throughout the day, and inability to take them in luggage when traveling for flight safety reasons. Thus, there is a need for alternate ways to remedy asthma attack symptoms.

Other diseases that can lead to lower oxygen saturation include chronic obstructive pulmonary disorder (COPD), mesothelioma, anemia, asthma, a blood clot in the lung (pulmonary embolism), a collapsed lung, congenital heart defects or disease, fluid in the lung (pulmonary edema), high altitude sickness, interstitial lung disease, medications that lower breathing rate (such as some narcotics and anesthetics), lung inflammation by toxic agents such as nitrogen dioxide gas, scarring in the lungs (pulmonary fibrosis), sleep apnea, and pneumonia. Chronic hypoxia (characterized by incidences of SpO2 of less than 95% over a period of weeks to months), experienced by post COVID-19 patients as well as other diseases and conditions, can lead to a slew of other diseases. For example, chronic hypoxia is known to increase blood pressure (see Calbet, "Chronic hypoxia increases blood pressure and noradrenaline spillover in healthy humans", *J Physiol*. 2003, 551(Pt 1): 379-386). Other conditions caused by chronic hypoxia include, but are not limited to, depression and other mood disorders, fatigue, headache, confusion, high blood pressure (hypertension), pulmonary hypertension, increased heart rate (tachycardia), heart failure, acute respiratory failure, and secondary polycythemia (an abnormal increase in the number of red blood cells). Thus, treating hypoxia could prevent, treat, or cure any of those conditions.

An effective, safe method of treating patients suffering from hypoxia, preferably in an in-patient or at-home environment and at a manageable cost, with no requirement for complicated equipment or specialized stuff (such as an per-os (oral ingestion) administration treatment) is sorely missing and desperately needed during COVID-19 times.

SUMMARY

Generally, the disclosure is directed to methods of treating a respiratory illness comprising: administering to the subject an effective amount of elemental metal and administering to the subject an effective amount of a source of nitrate anion ($NO_{3-}$). In some aspects, the subject is administered a composition comprising an elemental metal and a source of nitrate anion ($NO_{3-}$). In some aspects, an amount of nitrite ion ($NO_{2-}$) is administered in combination with the nitrate ion or even in place of the nitrite ion. The elemental metal is an alkaline earth metal, an alkali metal, or a transition metal. In some embodiments, the elemental metal is elemental magnesium, elemental calcium, elemental lithium, elemental zinc, or elemental iron. In preferred embodiments, the elemental metal is metallic (uncharged) magnesium and/or zinc. In some aspects, the source of nitrate anion is a salt of nitric acid, for example potassium nitrate, sodium nitrate, or magnesium nitrate. In yet other aspects, the source of nitrate anion is a botanical nitrate source. If a source of nitrite anion is also added in the formula, it can be in the form of various nitrite salts, such as sodium nitrite, potassium nitrite and the like, or even from fermented plant nitrate that has been reduced by nitrate reducing bacteria to nitrite. Dilute solutions of nitric acid could also be utilized, but are not preferred, due to their corrosive action and other impractical concerns, like the chemical incompatibilities of nitric acid and the ability of nitric acid solutions to produce nitrogen dioxide fumes. In certain implementations, the composition further comprises an acid.

In some implementations and for the exemplary purposes of this disclosure, the method includes orally administering to a human subject at least one elemental metal; and orally administering to the human subject a nitrate ($NO_3^-$), a nitrite ($NO_2^-$), or both. The elemental metal is selected from the group consisting of: elemental magnesium, elemental calcium, elemental lithium, elemental zinc, elemental sodium, elemental potassium, elemental beryllium, elemental rubidium, elemental cesium, elemental aluminum, elemental gallium, elemental indium, elemental tin, elemental bismuth, elemental scandium, elemental titanium, elemental vanadium, elemental chromium, elemental manganese, elemental cobalt, elemental manganese, elemental scandium, elemental titanium, nickel, elemental copper, elemental zinc, elemental yttrium, elemental zirconium, elemental niobium, elemental molybdenum, elemental technetium, elemental ruthenium, elemental rhodium, elemental palladium, elemental silver, elemental cadmium, elemental lanthanum, elemental hafnium, elemental tantalum, elemental tungsten, elemental rhenium, elemental osmium, elemental iridium, elemental platinum, elemental gold, and elemental manganese.

Particular implementations may include one or more or all of the following.

Further, orally administering to the human subject a pharmaceutically effective amount of an acid.

The human subject is administered a nitrate salt and/or a nitrite salt and the human subject is administered citric acid as the acid. The human subject is administered potassium nitrate and/or potassium nitrite.

The human subject has a blood oxygen saturation level (SpO2 level) of less than about 95% or less than about 92%. The oral administration of the at least one elemental metal and the nitrate and/or the nitrate to the human subject is repeated within 1 hour, 2 hours, 3 hours, 4 hours, 6 hours, 8 hours, 12 hours, 24 hours, 36 hours, 48 hours, 72 hours, or 96 hours of the initial oral administration. The human subject is orally administered the at least one elemental metal when the SpO2 level of the human subject falls below about 95% or about 92%.

The SpO2 level of the human subject increases by at least about 1% within about 5 minutes to about 2.5 hours after the administration of the at least one elemental metal and the nitrate and/or the nitrite.

The SpO2 of the human subject increases to at least about 94% within about 5 minutes to about 2.5 hours after of the administration of the at least one elemental metal and the nitrate and/or the nitrite.

The SpO2 of the human subject increases to at least about 95% within about 5 minutes to about 2.5 hours after of the administration of the at least one elemental metal and the nitrate and/or nitrite.

The human subject has Coronavirus disease (COVID-19).

The human subject has hypoxia after recovery from a SARS-CoV-2 infection.

The human subject has a condition selected from the group consisting of: SARS-Cov-2 infection, hypoxia after Coronavirus disease (COVID-19), acute respiratory distress syndrome (ARDS), post-ARDS hypoxia, pneumonia, chronic obstructive pulmonary disorder (COPD), mesothelioma, anemia, asthma, pulmonary embolism, collapsed lung, congenital heart defects or disease, pulmonary edema, high altitude sickness, interstitial lung disease, low breathing rate, lung inflammation, pulmonary fibrosis, sleep apnea, gastrointestinal infection, *Heliobacter pylori* infection, and a respiratory infection. Wherein the human subject has a viral respiratory infection. Wherein the human subject is hypoxic.

The human subject exhibits at least one symptom selected from the group consisting of: tissue damage, muscle aches, body aches, fatigue, sore throat, shortness of breath, difficulty breathing, chest pain, lung inflammation, cough, fever, anosmia, dysgeusia, sinus congestion, runny nose, decreased blood oxygen saturation, headache, gastrointestinal disturbances, nausea, vomiting, diarrhea, tiredness, inability to exercise, inability to work, inability to perform sexual activity, burnout, collapse, exhaustion, frazzle, lassitude, prostration, weariness, fatigue, worsening of symptoms after physical or mental activities, difficulty thinking or concentrating, cough, stomach pain, fast-beating or pounding heart, joint pain, pins-and-needles sensation, sleep problems, dizziness on standing, rash, mood changes, mood disorders, changes in menstrual period cycles, hypertension, depression, increased heart rate, heart failure, and acute respiratory failure. Wherein the tissue damage is in the brain, heart, lung and/or kidney. Wherein the administration of the at least one elemental metal and the nitrate and/or nitrite alleviates the at least one symptom in the human subject.

The human subject is orally administered a composition comprising the at least one elemental metal and the nitrate and the composition includes about 1 mg to about 2000 mg of the at least one elemental metal and about 30 mg to about 4000 mg of the nitrate. Wherein the composition includes elemental magnesium and/or elemental zinc.

The human subject is orally administered a composition including: about 1200 mg potassium nitrate; about 200 mg elemental magnesium; and about 50 mg elemental zinc. Wherein the composition further includes about 1000 mg citric acid. Wherein the composition is provided in one or more capsules. Wherein capsules have a size of 0 or smaller. Wherein the elemental metal magnesium has a mesh size of 60 to 200 and the elemental metal zinc has a mesh size of 325 or lower.

The human subject is administered the nitrite, and the amount of nitrite is administered is about 5 mg to about 300 mg, about 10 mg to about 200 mg, or about 30 mg and about 100 mg.

The oral administration of the nitrite does not cause the human subject to develop methemoglobinemia.

Further, orally administering to the human subject at least one gastric acid secretagogue. Wherein the at least one gastric acid secretagogue is selected from the group consisting of: caffeine, theophylline, theobromine, an ethanol solution, pentagastrin, and a cholinergic agent. Wherein the ethanol solution has 2%-14% ethanol. Wherein the cholinergic agent is selected from acetylcholine and pilocarpine.

The human subject is administered a composition comprising the at least one elemental metal and the nitrate and/or the nitrite, and composition is in a sustained release formulation.

In some implementations and for the exemplary purposes of this disclosure, the composition for human consumption includes: at least one elemental metal at a mesh size equal to or greater than 35, wherein the elemental metal is selected from the group consisting of: elemental magnesium, elemental calcium, elemental zinc, elemental copper, and elemental iron; and a nitrate ($NO_3^-$), a nitrite ($NO_2^-$), or both.

Particular implementations may include one or more or all of the following.

The mesh size of the elemental metal is 40 or greater.

The nitrate and the nitrite are an inorganic salt.

The composition includes: about 1 mg to about 800 mg of the elemental metal; and about 30 mg to about 2000 mg of the nitrate and/or the nitrite.

The at least one elemental metal is elemental magnesium at a mesh size between 60 and 200.

The composition is in a dosage form selected from capsules, cachets, pills, tablets, powders, granules, pellets, beads, particles, troches, and pastilles. The elemental metal is packaged with the nitrate and/or the nitrite.

The composition further comprising an acid. Wherein the composition includes the acid at an amount of about 50 mg to about 20,000 mg. Wherein the acid is packaged separately from the elemental metal and the nitrate and/or the nitrite.

Wherein the elemental metal, the nitrate, the nitrate, and the acid are in solid forms.

The composition further comprising a gastric acid secretagogue. Wherein the gastric acid secretagogue is in an amount sufficient enough to decrease gastric pH.

The elemental metal and the nitrate and/or nitrite are in a sustained release formulation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
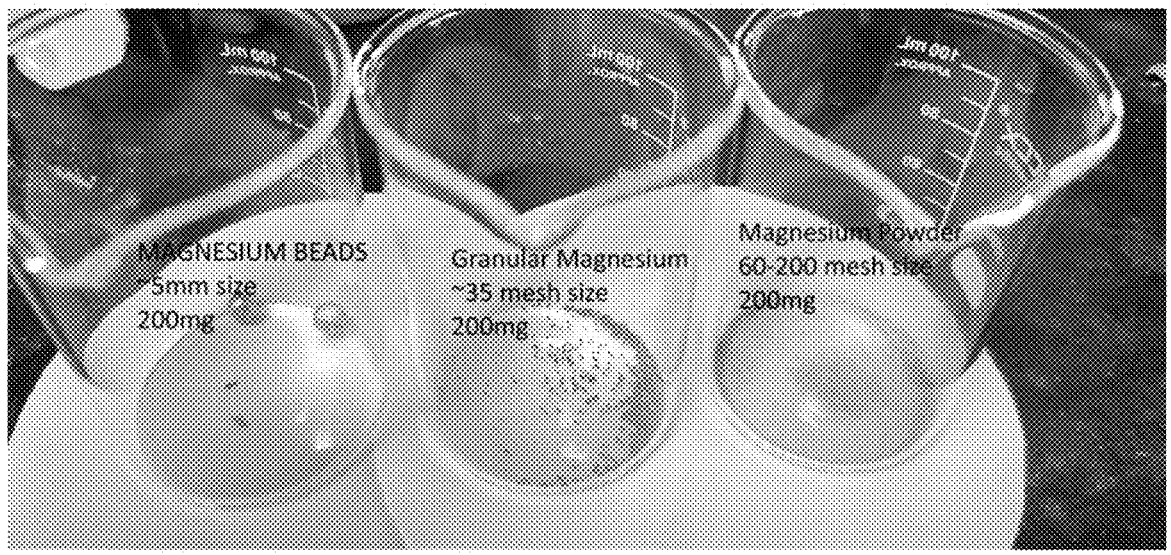
FIG. 1 depicts the three different forms of elemental magnesium tested in experiments.

Detailed aspects and applications of the disclosure are described below in the following detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant art, that implementations of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

As used herein, the term "about" refers to a deviation no more than 5% of the given value, for example a deviation of 3%, 2%, 1%, 0.5%, or 0.1% of the given value.

As referred to herein, "prevention", "prevent", and/or "preventing", which are used interchangeably herein, are intended to refer to all processes wherein there may be a slowing, interrupting, arresting, controlling, stopping, alleviating symptoms or complications or reversing of the progression of a respiratory illness or disease.

As used interchangeably herein, "treatment" and/or "treating" and/or "treat" are intended to refer to all processes wherein there may be a slowing, interrupting, arresting, controlling, stopping, alleviating symptoms or complications or reversing of the progression of a respiratory illness or disease.

As used herein, the term "acceptable" is a phrase used in its broadest sense and may describe ingredients of a composition that meet Food and Drug Administration (FDA) standards, United States Pharmacopeia (USP) standards, US Department of Agriculture (USDA) standards for food-grade materials, commonly accepted standards of the nutritional supplement industry, industry standards, botanical standards, or standards established by any recognized organization. These standards may delineate acceptable ranges of aspects of ingredients of a composition such as edibility, toxicity, pharmacological effect, or any other aspect of a chemical, composition, or preparation used in implementations of a composition.

As used herein, the term "composition" refers to both a mixture of ingredients or constituents as well as a combination of capsules or tablets that contains different ingredients or constituents. Accordingly, in certain embodiments, a composition encompasses separate capsules, tablets or other dosage forms that are packaged together and are meant to be taken together. For example, the nitrate/nitrite constituent and the elemental metal constituent could be in separate capsules, tablets and the like.

As used herein, the term "elemental metal" refers to the neutral-charged state of a metal element, in other words, a metal in its elemental form and not in a salt form or charged form (non-limiting exemplary salt forms and charged forms include the oxide, hydroxide, carbonate, chloride, lactate, citrate, aspartate, glycinate, and gluconate of the metal). As such, as used herein, elemental metals and salts of the same metal are different constituents. To be clear, as used herein, elemental metals (i.e. in their uncharged, metallic form) and ionic (charged) forms of the same metal (such as salts, oxides and hydroxides) are different constituents. A description that a composition comprises an elemental metal cannot be satisfied by the presence of a metal salt, and vice versa. For example, a composition that consists of magnesium citrate is not a composition that comprises elemental magnesium in spite of any description that magnesium citrate provides some amount of elemental magnesium. The elemental metals described herein include elemental magnesium, elemental calcium, elemental lithium, elemental zinc, elemental sodium, elemental potassium, elemental beryllium, elemental rubidium, elemental cesium, elemental aluminum, elemental gallium, elemental indium, elemental tin, elemental bismuth, elemental scandium, elemental titanium, elemental vanadium, elemental chromium, elemental manganese, elemental cobalt, elemental manganese, elemental scandium, elemental titanium, nickel, elemental copper, elemental zinc, elemental yttrium, elemental zirconium, elemental niobium, elemental molybdenum, elemental technetium, elemental ruthenium, elemental rhodium, elemental palladium, elemental silver, elemental cadmium, elemental lanthanum, elemental hafnium, elemental tantalum, elemental tungsten, elemental rhenium, elemental osmium, elemental iridium, elemental platinum, elemental gold, elemental manganese, and elemental iron. In preferable compositions for the treatment of respiratory illness, the elemental metal is chosen from the group of elemental metal magnesium and elemental metal zinc.

In some aspects, the present disclosure relates to the discovery that orally administering a source of nitrate anion ($NO_{3-}$) and an elemental metal to a subject with a respiratory illness can reduce or alleviate the symptoms associated with respiratory illness. It was surprisingly discovered that administration of a source of nitrate anion ($NO_{3-}$) and an elemental metal to a subject diagnosed with COVID-19 alleviated the subject's symptoms of chest pain, fever, muscle pain, cough, difficulty breathing and shortness of breath. In one implementation, the subject was administered a capsule comprising potassium nitrate ($KNO_3$), elemental magnesium, and elemental zinc while experiencing low blood oxygen saturation (between 90-92%). Within a half an hour of ingesting the capsule, the subject reported great relief from shortness of breath, chest pain, and breathing difficulties. The blood oxygen saturation level also rose to 97% within half an hour. The effect on blood oxygen saturation was reduced four hours after ingesting the capsule, but administration of a second capsule restored the subject's oxygen saturation level to normal (between 97% and 100%). In some embodiments, administering a source of nitrate anion and an elemental metal to a subject with a respiratory illness can speed up recovery from a respiratory illness.

These results were highly surprising as previous experiments utilizing nitrate alone at 409 mg and 479 mg doses failed to produce any increase in oxygen saturation (Rosetti et al., "Dietary nitrate supplementation increases acute mountain sickness severity and sense of effort during hypoxic exercise", *J Appl Physiol* (1985), 2017, 123(4): 983-992, Barlow et al., "The effect of a dietary nitrate supplementation in the form of a single shot of beetroot juice on static and dynamic apnea performance" *J Sport Nutr Exerc Metab*, 2018, 28(5): 497-501). It was also discovered that the combination of an elemental metal and a source of nitrate anion can instantly produce nitric oxide gas as well as increase lung excretion of nitric oxide. Administration of this combination was effective within minutes to increased leg press weight and time to exhaustion. The subjects testing the combination also reported that they felt it was easier to breath during physical activity. Thus, administering a combination an elemental metal and a source of nitrate anion provides relief to subjects suffering from low oxygen saturation level, breathing difficulties, chest pains, and shortness of breath.

The present disclosure relates to the discovery that the mesh size of an elemental metal used for producing nitric oxide (NO) when combined in a solution an acid and nitrate anion affects the therapeutic efficacy of the NO produced and administered to a subject in need of NO therapy.

The term "mesh" describes the size of an abrasive particle. When the mesh size (or grade) of a particle is reported, it reports the mean or average diameter of particles in that mesh size or grade. When two numbers are used in reference to the mesh size of a particle, this indicates that all of the particles in that grade of product are within that range of mesh sizes (i.e., mesh size 80-100).

U.S. mesh size (or U.S. sieve size) is defined as the number of openings in one square inch of a screen. For example, a size 36 mesh screen will have 36 openings while a size 150 mesh screen will have 150 openings. The size of screen (one square inch) is constant, so a higher mesh number will mean a smaller screen opening and thus refer to smaller particles. Generally, a U.S. mesh size is measured using screens down to size 325 mesh (325 openings in one square inch). Sometimes the mesh size of a product is noted with either a minus (−) or plus (+) sign. These signs indicate that the particles are either all smaller than (−) or all larger than (+) the mesh size. For example, a product identified as −100 mesh would contain only particles that passed through a 100 mesh screen. A +100 grade would contain particles that did not pass through a 100 mesh screen. When a grade of product is noted with a dash or a slash it indicates that the product has particle contained within the two mesh sizes. For example, a 30/70 or 30-70 grade would only have particles that are smaller than 30 mesh and larger than 70 mesh.

Table 1 depicts a mesh conversion chart, which shows the approximate size in inches and microns for various mesh sizes. These values are generally accepted as accurate but are approximates, because the thickness of the wire used to make a specific screen will vary the number of openings in the one square inch. Most grades below 325 mesh are indicated by the micron size as these sizes are not manufactured using screens.

TABLE 1

Mesh conversion chart.

| US Mesh | Micron | Inches |
|---|---|---|
| 4 | 4,750 | 0.187 |
| 5 | 4,000 | 0.157 |
| 6 | 5,350 | 0.132 |
| 7 | 2,800 | 0.111 |
| 8 | 2,360 | 0.0937 |
| 10 | 2,000 | 0.0787 |
| 12 | 1,700 | 0.0661 |
| 14 | 1,400 | 0.0555 |
| 16 | 1,200 | 0.0473 |
| 18 | 1,000 | 0.0394 |
| 20 | 850 | 0.0331 |
| 24 | 690 | 0.027 |
| 30 | 560 | 0.022 |
| 36 | 485 | 0.019 |
| 40 | 425 | 0.016 |
| 46 | 355 | 0.014 |
| 54 | 305 | 0.012 |
| 60 | 250 | 0.01 |
| 70 | 210 | 0.0083 |
| 80 | 165 | 0.0065 |
| 90 | 145 | 0.0057 |
| 100 | 149 | 0.0059 |
| 120 | 125 | 0.0049 |
| 140 | 105 | 0.0041 |
| 150 | 89 | 0.0035 |
| 170 | 88 | 0.0031 |
| 180 | 76 | 0.003 |
| 200 | 75 | 0.0029 |
| 220 | 63 | 0.0025 |
| 240 | 53 | 0.002 |
| 280 | 44 | 0.0015 |
| 320 | 36 | 0.0012 |
| 400 | 23 | 0.00087 |
| 500 | 19 | 0.00075 |
| 600 | 16 | 0.00065 |
| 800 | 12 | 0.00047 |

TABLE 1-continued

Mesh conversion chart.

| US Mesh | Micron | Inches |
|---|---|---|
| 1,000 | 9 | 0.00028 |
| 1,200 | 6 | 0.00024 |

It was surprisingly discovered that elemental metals of mesh size greater than 35 and equal to or less than 325 mesh size produce the most therapeutic effect while limiting the amount of side effects experienced (such as gastrointestinal disturbances, nausea, vomiting, heartburn) after administration of a composition, comprising at least one elemental metal and a source of nitrate anion ($NO_{3-}$) or nitrite anion ($NO2-$). Depending on the metal and the reactivity of it with the nitrate or nitrite ion and acid, different mesh sizes may be preferable, but generally mesh sizes of 40-325 produce the better therapeutic effects in the case of magnesium and zinc, with optimal mesh size for magnesium 60-200 (what is commonly called magnesium metal powder) and optimal mesh size for zinc 325 or greater (what is commonly called zinc dust). In some aspects, the administration of the composition of elemental metal and nitrate and/or nitrite, comprises orally administering to the subject at least one elemental metal of mesh size 35 or greater and orally administering to the subject a source of nitrate and/or nitrite anion. In some other aspects, the administration of the composition comprises orally administering to the subject at least one elemental metal of mesh size 35 or greater and orally administering to the subject a source of nitrate and/or nitrite anion and an acid (such as citric acid), with the acid preferably in a separate dosing form (like a capsule, powder or tablet). The administration of the composition of elemental metal and nitrate or nitrite anion, or the composition of elemental metal and nitrate and/or nitrite anion and an acid (such as citric acid) improved alertness, energy levels, cured headache/migraine, increased athletic performance as exhibited by increased strength and endurance, and reduced the symptoms of a respiratory illness (for example, shortness of breath, breathing problems, chest pain, lung inflammation and/or decreased oxygen saturation) with a shorter period of time after administration than administration of the composition where the mesh size of the elemental metal is not between 40 and 325. Subjects also experienced greater relief from respiratory symptoms when administered a composition of elemental metal and nitrate or nitrite anion, or the composition of elemental metal and nitrate or nitrite anion and an acid (such as citric acid) where the mesh size of the elemental metal is between 40 and 200. In some embodiments, the gastrointestinal side effects associated with ingestion of the composition (for example, gastrointestinal disturbances, diarrhea, nausea, heartburn and vomiting) were reduced when the composition contains elemental metal with mesh sizes greater than 35.

In some implementations, the nitrate/nitrite constituent(s) and the elemental metal constituent(s) are in separate capsules, tablets, and the like as oral dosage forms.

Other methods the inventors have discovered that can prevent the occurrence of side effects include:
Ingesting the capsules with a sufficient amount of water, preferably cold (below room temperature), in an amount of at least 500 ml;
Avoiding ingesting the capsules in a fasted stomach state (no presence of food in the stomach, usually achieved by adhering from ingestion of food for at least 8 hours); and
Consumption of milk or other neutral to alkaline products in cases of extreme discomfort after the ingestion of the formulation.

As shown in the examples, under acidic conditions achievable safely in the human stomach, granular magnesium reacts too slowly and produces very little NO to achieve an appreciable/observable therapeutic effect. Although there is no known mechanism by which NO gas could have a systematic effect on the body or reach the lungs, it was observed by the inventors that reduced NO gas production in the stomach was correlated with reduced or absent therapeutic effects of the ingested formulations. It is also of concern that low mesh granular magnesium might not be able to fully react before it leaves the stomach and gets wasted. To prove this, the inventors added 200 mg of granular (mesh size 35) elemental metal Magnesium in simulated gastric acid fluid (100 ml 0.1N HCl in water) with 200 mg of Elemental metal granular Magnesium and 1000 mg of Citric Acid. On normal gastric emptying conditions, less than 60% of the ingested compound/meal exists in the stomach at 2 hours, and less than 10% at 4 hours (Banks K P, Syed K, Parekh M, et al. Gastric Emptying Scan. [Updated 2020 Dec. 22]. In: StatPearls [Internet] Treasure Island (FL): StatPearls Publishing; 2021 Jan-. Available from: https://www.ncbi.nlm.nih.gov/books/NBK531503/). Even 4 hours later, granules of elemental metal Magnesium could be spotted at the bottom of the beaker. On the other hand, magnesium dust reacts too rapidly with the nitrate and acid of the formula and creates too much NO (toxic by itself in 100+ ppm) that also rapidly oxidizes to highly toxic and potentially lethal $NO_2$. The experiment with magnesium dust created so much NO and $NO_2$ that the gas produced pushed both gas sensors to the maximum toxic level in the chamber in less than one minute (250 ppm NO and 100 ppm $NO_2$). The solution also increased rapidly in heat (the 100 ml solution reached over 80 C from an ambient temperature of 30 C) which would cause damage and burns to tissues such as the gastric epithelium. Thus, the magnesium dust would be outright toxic to any human and would be inappropriate for therapeutic uses in these quantities. On the other hand, magnesium powder (mesh size 60-200) produces NO sustainably for over 1 hour and achieved a maximum concentration of 39.8 ppm NO with zero production of $NO_2$, which is a novel scientific breakthrough, previously unheard of in therapeutics. Zinc, being less reactive than magnesium, was used at a mesh size of dust (325 mesh) and can produce NO sustainably for over 4 hours (which is one of the recommended time periods between the administration of the disclosed therapeutic compositions).

Accordingly, disclosed herein are compositions comprising an elemental metal with a mesh size of greater than 35 and a source of nitrate anion or nitrite anion. In some aspects, the mesh size of the elemental metal is also less than 200. For example, in particular embodiments, the composition comprises elemental metal with a mesh size of between 40 and 200 and the source of nitrate anion or nitrite anion. In some implementations, the source of nitrate anion or nitrite anion is a nitrate salt or nitrite salt, for example, potassium nitrate, sodium nitrate, amino acid nitrate, potassium nitrite, amino acid nitrite or sodium nitrate. In other implementations, the source of the nitrate anion or nitrite anion is a botanical source, for example, beetroot extract or *Amaranthus* extract.

Disclosed herein are methods for treating a respiratory illness comprising administering to the subject an effective amount of elemental metal and administering to the subject an effective amount of a source of nitrate anion. In some implementations, the subject is administered a composition comprising an elemental metal and a source of nitrate anion. In some embodiments, the subject is also administered an acid. The acid is administered to ensure the pH of the stomach upon ingestion of the claimed composition remains acidic. In some implementations, the acid is administered in a separate composition from the elemental metal and the source of nitrate anion. Thus, in some implementations, the subject is administered a first composition comprising the elemental metal and the source of nitrate anion and a second composition comprising the acid. Accordingly, the subject is administered a therapeutic regime comprising a dosage form comprising the elemental metal and the source of nitrate anion (for example, a capsule, tablet, or pill) and another dosage form comprising the acid (for example, a in a solid form such as a capsule, tablet, or pill or a liquid form). In other implementations, the elemental metal, the source of nitrate anion, and the acid are administered in dosage forms (for example, capsules or tablets) that comprise these three constituents. In certain embodiments, instead of administering a source of nitrate anion, a source of nitrite anion is administered. In other embodiments, the subject is administered both a source of nitrate anion and a source of nitrite anion.

In certain implementations, the subject exhibits at least one symptom selected from the group consisting of shortness of breath, breathing problems, chest pain, lung inflammation, and decreased oxygen saturation. In some aspects, the subject has a respiratory infection. In some cases, the subject has a viral infection and/or a bacterial infection. For example, an infection by a coronavirus, an influenza virus, respiratory syncytial virus, *Streptococcus pneumoniae, Haemophilus influenzae* type b (Hib), and/or *Pneumocystis jiroveci*. In some implementations, the subject is diagnosed with pneumonia or a severe acute respiratory syndrome caused by a coronavirus, for example an alpha coronavirus selected from 299E and NL63 or a beta coronavirus selected from OC43, HKU1, MERS-CoV, SARS-CoV, or SARS-CoV-2. In some aspects, administering an effective amount of elemental metal and an effective amount of a source of nitrate anion reduces the symptoms of shortness of breath, breathing problems, chest pain, lung inflammation and/or decreased oxygen saturation in the subject. In certain implementations, the elemental metal and the source of nitrate anion are administered to the subject every four hours. In some aspects, the repeated administration continues until at least one of the symptoms vanish, for example, for at least two days or four days.

In other aspects, the subject has a respiratory fungal infection, like aspergillosis. In some aspects, the subject has a protozoa respiratory infection and symptoms, such as direct damage to the parenchyma (e.g. toxoplasmosis); through a systemic inflammatory response by haematogenous dissemination (e.g. malaria); and contiguity with an adjacent lesion (e.g. amoebiasis). In some aspects, the subject has inflammation to the lungs due to toxic agents, such as Nitrogen Dioxide. In some aspects, the subject may have inflammation of the lungs and subsequent breathing problems of unknown cause.

In certain implementations, the subject exhibits at least one symptom selected from the group consisting of shortness of breath, breathing problems, chest pain, lung inflammation, and decreased oxygen saturation. In some aspects, the subject has a respiratory infection. For example, an infection by a coronavirus, an influenza virus, respiratory syncytial virus, *Streptococcus pneumoniae, Haemophilus influenzae* type b (Hib), and/or *Pneumocystis jiroveci*. In some implementations, the subject is diagnosed with a severe acute respiratory syndrome caused by a coronavirus, for example an alpha coronavirus selected from 299E and NL63 or a beta coronavirus selected from OC43, HKU1, MERS-CoV, SARS-CoV, or SARS-CoV-2. In some aspects, administering an effective amount of elemental metal and an effective amount of a source of nitrate or nitrite anion reduces the symptoms of shortness of breath, breathing problems, chest pain, lung inflammation and/or decreased oxygen saturation in the subject. In certain implementations, the elemental metal and the source of nitrate or nitrite anion are administered to the subject every four hours. The frequency of administration will depend on the potency of the dose, however. For example. frequency and/or amount of dose can be altered according to disease and symptom severity progression or as instructed by an overseeing medical professional. For example a patient with early onset COVID-19 and mild symptoms (SpO2 between 93-94) may require half a dosage or dosage administered every 4 or 8 hours. A severe COVID-19 case that has progressed to extensive lung damage (SpO2 below 85) may require double dosage, or dosing every 2 hours, or even more. In some aspects, the repeated administration continues until at least one of the symptoms vanish, for example, for at least two days or four days or longer.

Also disclosed are methods of increasing blood oxygen saturation level in a subject; reducing cough in a subject; reducing migraine and headache pain in a subject; reducing gastrointestinal disturbance (for example, diarrhea, nausea and/or vomiting, a *Helicobacter pylori* infection, an ulcer, or irritable bowel syndrome) in a subject; reducing fever in a subject; reducing shortness of breath or difficulty breathing in a subject; reducing muscle and body aches in a subject; reducing loss of smell and taste in a subject; reducing sore throat in a subject; reducing congestion or runny nose in a subject; reducing fatigue in a subject; reducing chest pain in a subject; and reducing organ damage caused by low blood oxygen level in a subject.

The elemental metal is an alkaline earth metal, an alkali metal, or a transition metal. Because elemental metals are reactive, they are not found in nature. Rather they exist as ores which contain a mixture of various metallic compounds such as salts and oxides. As such, complex extraction and purification utilizing physicochemical methods is required to produce elemental metals. In some embodiments, the elemental metal is elemental magnesium, elemental calcium, elemental lithium, elemental zinc, elemental sodium, elemental potassium, elemental beryllium, elemental rubidium, elemental cesium, elemental aluminum, elemental gallium, elemental indium, elemental tin, elemental bismuth, elemental scandium, elemental titanium, elemental vanadium, elemental chromium, elemental manganese, elemental cobalt, elemental manganese, elemental scandium, elemental titanium, nickel, elemental copper, elemental zinc, elemental yttrium, elemental zirconium, elemental niobium, elemental molybdenum, elemental technetium, elemental ruthenium, elemental rhodium, elemental palladium, elemental silver, elemental cadmium, elemental lanthanum, elemental hafnium, elemental tantalum, elemental tungsten, elemental rhenium, elemental osmium, elemental iridium, elemental platinum, elemental gold, elemental manganese or elemental iron. In some embodiments, the elemental metal is selected from the group consisting of: elemental magnesium, elemental calcium, elemental lithium, elemental zinc, and elemental iron. In some embodiments, the subject is administered a combination of elemental metals. Thus, in some aspects, the composition administered to the subject comprises more than one elemental metal. The element metal may be in any form, for example, a powder or granules, or any other form wherein the metal remains uncharged before combining with the nitrate and the acid.

In some aspects, the nitrate anion ($NO_3^-$) is a nitrate salt of an amino acid or amino acid or an amino acid derivative (for example, creatine nitrate, arginine nitrate, carnitine nitrate, n-acetyl carnitine nitrate, citrulline nitrate, betaine nitrate, and proline nitrate), an inorganic nitrate salt (for example, magnesium nitrate, sodium nitrate, potassium nitrate, calcium nitrate, and lithium nitrate, or their mixed salts, co-crystalline formulation and hydrates), or a natural nitrate source. For natural nitrate sources, the nitrate has been concentrated and/or isolated from a natural source, such as a botanical nitrate source. Examples of natural nitrate sources include, but are not limited to, beet juice, beet juice powder, concentrated beet juice powder, celery powder, spinach and red spinach extract, and *Amaranthus* extract. In preferred implementations, the nitrate content of natural nitrate sources is standardized so as to provide the sufficient amount of nitrate. In some aspects, the composition comprises more than one source of nitrate anion.

In some aspects, the nitrite anion ($NO_2^-$) is a nitrite salt of an amino acid or a salt of an amino acid derivatives (for example, creatine nitrite, arginine nitrite, carnitine nitrite, n-acetyl carnitine nitrite, citrulline nitrite, betaine nitrite, and proline nitrite), an inorganic nitrite salt (for example, magnesium nitrite, sodium nitrite, potassium nitrite, calcium nitrite, and lithium nitrite, or their mixed salts, co-crystalline formulation and hydrates), or a natural nitrite source. For natural nitrite sources, the nitrite has been concentrated and/or isolated from a natural source, such as a botanical nitrite source.

In some embodiments, the elemental metal and nitrate and/or nitrite anion are contained in a system for sustained release of NO. For example, the system may be a time-released system (such as a diffusion system, a dissolution system, an osmotic system, and ion-exchange resin, or any other effective time-release system), a floating system, a bio-adhesive system, or a matrix system where exposure to the acid or acid solution is controlled. In other implementation either mechanical or electronic methods may be utilized to release the metal and nitrate or nitrite into the acid solution in a continuous manner to allow for sustained NO gas release.

In some implementations, the method comprises providing the acid in powder form mixed with the nitrate or nitrite anion and/or the elemental metal before dissolving in a solvent so that NO gas is produced. The acid in powdered formed may be, for example, citric acid, malic acid, or fumaric acid. In preferred embodiments, the solvent used is water, as it is safe, non-toxic, readily available. However other protic and/or polar solvents could be utilized such as ammonia, ethanol, acetic acid and the like. The water or solvent need not be pure and other compounds can be dissolved into it, such as aromas, scents, other medicine and the like. In some embodiments, the acid is a salt of a strong acid with a weak base, which when dissolved in water or some other polar protic solvent, results in the formation of an acidic solution. Thus, the acid may be ammonium chloride, ammonium nitrate, or creatine nitrate. In certain implementations, where the nitrate or nitrite anion is provided as a nitrate or nitrite salt formed with weak bases (such as creatine or proline, the nitrate or nitrite salt can serve as the source for both the acid and the nitrate or nitrite anion.

It will be understood that although the usual sequence of adding the ingredients of the formula is first creating an acid solution and then adding simultaneously the elemental metal and the nitrate or nitrite, there can be variations. For example, the step of combining a nitrate or nitrite anion and an elemental metal in an acidic solution may comprise simultaneously adding the nitrate or nitrite, the powdered acid, and the elemental metal in the water or comprise preparing a solution of a nitrate in water and then adding the acid and elemental metal. An important feature of the disclosed methods is that the elemental metal cannot be allowed to fully react with the acid before being combined with the nitrate, otherwise the elemental metal and the acid will form salts of the elemental metal and not produce NO gas. Thus if one was to add elemental magnesium in an acid solution, after the reaction was completed (which would be indicated by dissolution of the magnesium in the liquid in its salt form) no nitric oxide gas would form with the addition of a nitrate or nitrite anion.

Methemoglobinemia, a condition that could be monitored by a drop in $SpO_2$ levels, is a side effect associated with conventional inhaled NO therapy (Raut and Maheshwari, "Inhaled nitric oxide, methemoglobinemia, and route of delivery." *Saudi J Anaesth.* 2017, 11(3):364). It was surprisingly found that administration of the NO gas according to the method described herein did not result in the development of methemoglobinemia. The mechanism for why methemoglobinemia was not caused by the disclosed method remains in research, but the hydrogen gas product of the reaction of the nitrate or nitrite anion and elemental metal in the acidic solution is suspected to have a protective effect. It should be noted that the inventors believe that the prevention and treatment of methemoglobinemia is the result of this invention and that there are additional elemental metals can produce hydrogen by reacting with bases, for example, aluminum: $2Al+2NaOH+2H2O \rightarrow 2NaAlO2+3H$. One could have for the purposes of the invention NO gas created by reaction of nitrite or nitrate with an acid in one beaker and generation of $H_2$ gas by reaction of a metal that produces hydrogen in contact with bases in another beaker, such as aluminum.

During the experimental and development stage of this invention one of the inventors found himself exposed multiple times to NO levels higher than 25 ppm (measured with a BW BWS-N-Y yellow housing, Solo nitric oxide (NO) gas detector) and observed no ill effects. In fact, the inventor's oxygenation levels as measured by $SpO_2$ oximeter were always in the 97-100 range. Accordingly, also disclosed herein are methods of preventing the onset of methemoglobinemia from nitrate, nitrite, or NO exposure, wherein the method comprising administering hydrogen to the subject exposed to a source of nitrate, a source of nitrite, or NO.

In some embodiments, the amount of elemental metal and the amount of the source of nitrate or nitrite anion administered are between about 1 mg and about 2000 mg and between about 4 mg and about 4000 mg respectively. In certain embodiments, the subject is administered about 1 to about 900 mg elemental magnesium and a source of nitrate or nitrite anion providing about 5 to about 2000 mg of nitrate or nitrite anion, about 30 mg to about 4000 mg of nitrate or nitrite anion, or about 50 mg to about 4000 mg of nitrate or nitrite anion. In some aspects, the source of nitrate or nitrite anion provides about 30 mg to 2000 mg of nitrate or nitrite anion, about 50 mg to about 2000 mg of nitrate or nitrite anion, about 5 mg to about 1000 mg of nitrate or nitrite anion, about 30 mg to about 1000 mg of nitrate or nitrite anion, about 50 mg to about 1000 mg of nitrate or nitrite anion, about 5 mg to about 600 mg of nitrate or nitrite anion, about 30 mg to about 600 mg of nitrate or nitrite anion, about 50 mg to about 600 mg of nitrate or nitrite anion, about 5 mg to about 500 mg of nitrate or nitrite anion, about 30 mg to about 500 mg of nitrate or nitrite anion, or about 50 mg to about 500 mg of nitrate or nitrite anion.

In some aspects, the molar ratio of the source of nitrate or nitrite anion to the elemental metal administered to the subject is at least 2:1. The doses of the elemental metal and the source of nitrate or nitrite anion can be adjusted according to the subject's weight, age, and health status. In some embodiments, the amount of elemental metal in the composition is between 1 mg and 800 mg or between 5 mg and 400 mg. In some embodiments, the amount of the source of nitrate or nitrite anion is between 30 mg and 2000 mg or between 50 mg and 600 mg. In one embodiment, the composition comprises 100 mg of elemental metal and 250 mg of magnesium nitrate hexahydrate (corresponds to 60.5 mg of nitrate anion and 23.6 mg of Mg).

The acid is administered with the elemental metal and source of nitrate or nitrite anion to ensure the pH of the stomach upon ingestion of the claimed composition remains acidic. The acid component can be any acid suitable for human consumption, non-limiting examples include, citric acid, succinic acid, malic acid, ascorbic acid, or tartaric acid or any gastric acid inducing secretagogue. In some aspects, the acid is in a solid form, for example, a powder. Thus, the amount of the acid in the composition in some embodiments is between 50 mg and 20,000 mg, between 50 mg and 2000 mg, between 50 mg and 1000 mg, between 100 mg and 20,000 mg, between 100 mg and 2000 mg, between 100 mg and 1000 mg, between 200 mg and 20,000 mg, between 200 mg and 2000 mg, between 200 mg and 1000 mg, between 300 mg and 20,000 mg, between 300 mg and 2000 mg, between 300 mg and 1000 mg, between 500 mg and 20,000 mg, between 500 mg and 2000 mg, or between 500 mg and 1000 mg. In some aspects, the acid component of the composition is a vinegar. In some implementation, the disclosed composition does not comprise an acid, but the composition is administered with an acid or gastric acid inducing secretagogue. For example, the composition is co-administered with an acidic solution with pH between 2-6, for example, diluted vinegar or a solution of citric acid. In some aspects, the acidic solution is diluted acetic acid, nitric acid, sulfuric acid, and the like.

Where the subject is administered a composition comprising elemental metal and a source of nitrate or nitrite anion, the composition comprises an effective amount of the source of nitrate or nitrite anion and an effective amount of the elemental metal. The effective amount of the elemental metal enhances the effectiveness of the nitrate or nitrite anion in providing a beneficial effect. Accordingly, in some embodiments, the effective amount of the source of nitrate or nitrite anion is an amount sufficient to restore oxygen saturation level in a subject with low oxygen saturation.

In certain embodiments, the composition comprises 1 to about 900 mg elemental magnesium and a source of nitrate or nitrite anion providing about 5 to about 2000 mg of nitrate or nitrite anion, about 30 mg to about 4000 mg of nitrate or nitrite anion, or about 50 mg to about 4000 mg of nitrate or nitrite anion. In some aspects, the source of nitrate or nitrite anion provides about 30 mg to 2000 mg of nitrate or nitrite anion, about 50 mg to about 2000 mg of nitrate or nitrite anion, about 5 mg to about 1000 mg of nitrate or nitrite anion, about 30 mg to about 1000 mg of nitrate or nitrite anion, about 50 mg to about 1000 mg of nitrate or nitrite anion, about 5 mg to about 600 mg of nitrate or nitrite anion, about 30 mg to about 600 mg of nitrate or nitrite anion, about 50 mg to about 600 mg of nitrate or nitrite anion, about 5 mg to about 500 mg of nitrate or nitrite anion, about 30 mg to about 500 mg of nitrate or nitrite anion, or about 50 mg to about 500 mg of nitrate or nitrite anion.

In some aspects, the molar ratio of the source of nitrate or nitrite anion to the elemental metal in the composition is at least 2:1. The doses of the elemental metal and the source of nitrate or nitrite anion can be adjusted according to the subject's weight, age, and health status. Typically, normotensive subjects require less of elemental metal and nitrate or nitrite anion than hypertensive subjects, and hypotensive subjects will require even less elemental metal and nitrate or nitrite anion than normotensive subjects. In some embodiments, the amount of elemental metal in the composition is between 1 mg and 800 mg or between 5 mg and 400 mg. In some embodiments, the amount of the source of nitrate or nitrite anion is between 30 mg and 2000 mg or between 50 mg and 600 mg. In one embodiment, the composition comprises 100 mg of elemental metal and 250 mg of magnesium nitrate hexahydrate (corresponds to 60.5 mg of nitrate anion ($NO_3$) and 23.6 mg of Mg).

In some embodiments, the elemental metal in the composition is covered or microencapsulated with a suitable material that is poorly soluble in water but soluble in the acidic environment of the stomach, for example, magnesium oxide, cellulose polymers, alginates (such as calcium alginate), or aluminum hydroxide.

In certain embodiments, proline nitrate or nitrite is the source of nitrate or nitrite anion in the composition. In some embodiments, the magnesium nitrate or nitrite is the source of nitrate or nitrite anion in the composition. In such embodiments, the magnesium nitrate or nitrite may be anhydrous or hydrated. The degree of hydration of the magnesium nitrate or nitrite is between one and six molecules of water per molecule of magnesium or nitrite. In a particular embodiment, magnesium nitrate hexahydrate is the salt of nitric acid in the composition.

In some embodiments, the disclosed composition further comprises an acid. The acid component can be any acid suitable for human consumption, for example, citric acid, succinic acid, malic acid, ascorbic acid, or tartaric acid. In some aspects, the acid is in a solid form, for example, a powder. Thus, the amount of the acid in the composition in some embodiments is between 50 mg and 20,000 mg, between 50 mg and 2000 mg, between 50 mg and 1000 mg, between 100 mg and 20,000 mg, between 100 mg and 2000 mg, between 100 mg and 1000 mg, between 200 mg and 20,000 mg, between 200 mg and 2000 mg, between 200 mg and 1000 mg, between 300 mg and 20,000 mg, between 300 mg and 2000 mg, between 300 mg and 1000 mg, between 500 mg and 20,000 mg, between 500 mg and 2000 mg, or between 500 mg and 1000 mg. In some aspects, the acid component of the composition is a vinegar. In some implementation, the disclosed composition does not comprise an acid, but the composition is administered with an acid. For example, the composition is co-administered with an acidic solution with pH between 2-6, for example, diluted vinegar or a solution of citric acid. In some aspects, the acidic solution is diluted acetic acid, nitric acid, sulfuric acid, and the like. In some embodiments for patients that cannot ingest acidic substances due to health reasons, such as patients with gastric ulcer and GERD, the acid component could be replaced with a gastric acid secretagogue (a compound that will stimulate excretion of gastric acid in the stomach), like caffeine, bitter tasting compounds, ethanol (preferably at concentrations of 2-14%), or even a pharmaceutical agent like pentagastrin or cholinergic agents like acetylcholine and pilocarpine.

The disclosed composition may be in the form of a capsule, tablet, pill, liquid, liquid suspension, vapor, powder, granulate, pulverulence, or a combination thereof. In a preferred embodiment, the disclosed composition is in a solid form. In some embodiments, the elemental metal and the source of nitrate or nitrite anion, and in some aspects the acid, are combined into a capsule or a tablet. In other embodiments, the acid is in a separate tablet or capsule than the elemental metal and the source of the nitrate or nitrite ion. The enhanced activity of co-administration the source of nitrate or nitrite anion and the elemental metal are not reduced if the subject ingests the source of nitrate or nitrite anion and the elemental metal separately at different times, for example via co-administration of separate capsules of the source of nitrate or nitrite anion and the elemental metal. Accordingly, in some aspects, the composition described herein comprises a capsule comprises a source of nitrate or nitrite anion and a capsule comprising an elemental metal. In embodiments of the composition further comprising an acid, the composition further comprises a capsule comprising the acid.

It is notable that the powdered form of the disclosed composition loses its potency when all the components are combined fully reacted in water prior to ingestion. Accordingly, administration of the powdered form of the composition should take care to minimize exposure to water before immediate administration. For example, the subject should ingest the powdered composition and then wash it down with water instead of dissolving the powdered composition in water and drinking the mixture. Also, if the composition is added in an alkaline mixture (pH above 7), such as water mixed with baking soda, it can retain its effectiveness for at least 10 minutes before ingestion.

In a preferred embodiment utilized for the treatment of COVID-19 and other respiratory and cardiovascular diseases, the formulation comprises of a US size 000 gelatin capsule comprising 1200 mg $KNO_3$ FCC grade, 200 mg elemental metal Magnesium powder (mesh size 60-200), 50 mg elemental metal Zinc dust (mesh size about 325) and a separate US size 000 capsule comprising 1000 mg of anhydrous Citric Acid, food grade. In a separate preferred implementation, the above formula is instead contained in 2 (two) US size 0 capsules containing 600 mg $KNO_3$ FCC grade, 100 mg elemental metal Magnesium powder (mesh size 60-200), 25 mg elemental metal Zinc dust (mesh size about 325) and 2 (two) capsules comprising 500 mg of anhydrous Citric Acid each food grade. In certain cases, administration of the smaller size capsules can help prevent some of the side effects experienced by some of the patients, such as G.I. discomfort, nausea and vomiting. A subject could, for example ingest 2 (two) 000 capsules (i.e. one capsule containing the 1200 mg $KNO_3$+200 mg elemental metal Magnesium+50 mg Elemental Zinc capsule, refereed herein as the "SpO2max" and a second capsule containing the Citric Acid (CA). However, if the subject is experiencing stomach discomfort, then the subject could swallow 2 (two) size 0 capsules instead at half the dose but with double the frequency.

In one implementations of the method of treating a respiratory illness, the subject is orally administered one capsule comprising 100 mg-to 250 mg of elemental metals, 250 mg of magnesium nitrate hexahydrate (providing 60.5 mg of nitrate anion ($NO_{3-}$) and 23.6 mg of $Mg^+$), and 600 mg of anhydrous citric acid. In another implementation, the subject is orally administered composition comprises 1-2 g *Amaranthus* (providing 10-90% nitrate), 50-1000 mg vitamin C, 50-1000 mg magnesium oxide, 10-1000 mg L-cysteine, 50-1000 mg theanine, 5-100 mg elemental zinc, 0.5-30 mg folate/5-MTHF, and 1-500 mcg potassium molybdate.

In other implementations, the subject the administered three capsules where two of the capsules each comprise a source of nitrate or nitrite anion and the elemental metal while the remaining capsule comprises the acid. For example, the capsule comprising the source of nitrate or nitrite anion and the elemental metal contains proline nitrate or nitrite and elemental magnesium, while the capsule comprising the acid contains citric acid. In a particular embodiment, the composition comprises two capsules, each comprising 250-750 mg proline nitrate and 5-200 mg elemental magnesium, and one capsule comprising 250-1250 mg citric acid. As another example, the composition comprises a plurality of capsules that, when combined, provide 1-2 g *Amaranthus* (providing 10-90% nitrate), 50-1000 mg vitamin C, 50-1000 mg magnesium oxide, 10-1000 mg L-cysteine, 50-1000 mg theanine, 5-100 mg elemental zinc, 0.5-30 mg folate/5-MTHF, and 1-500 mcg potassium molybdate. In a preferred implementation, the vitamin C is in a separate capsule as the other constituents.

In some aspects, the composition further comprises a suitable pharmaceutically acceptable coating to prevent moisture from getting in the tablets and/or an additive. Non-limiting examples of the pharmaceutically acceptable coating include waxes, polymers, solid fatty acids, etc. Non-limiting examples of the additive include a carrier, excipient, binder, colorant, flavoring agent, preservative, buffer, diluent, and combinations thereof. In some aspects, the additive is a pharmaceutically acceptable additive or an acceptable food additive.

Although capsules are the preferred form of the composition, compositions and/or formulations of the present invention may be administered in any form, including one of a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary, cream, a gel, a paste, a foam, and combinations thereof for example. Compositions and/or formulations of the present invention may also include an acceptable additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a acceptable carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof).

Although oral ingestion is the preferred method of administration for the compositions described herein, other routes and forms of administration could be possible utilizing the methods and compositions described herein, including immediate release tablets or capsules (where the excipient disintegrates almost immediately in contact with the saliva or gastric fluid), delayed release tablets or capsules and the like, sustained release formulations (where one or more of the constituents of the formulation are released on the gastric tract over a long period of time), sublingual tablets, direct administration of the constituents via a catheter or feeding tube to the G.I. tract, buccal delivery and the like.

In certain implementations, the compositions and methods disclosed herein are used to prevent, treat, or alleviate one or more symptoms of a respiratory illness. Non-limiting examples such respiratory illnesses include pulmonary hypertension, lung cancer, COVID-19, acute respiratory distress syndrome (ARDS), asthma, cystic fibrosis, chronic obstructive pulmonary disease (COPD), pneumonia, interstitial lung disease, pulmonary fibrosis, acute lower respiratory infection, pulmonary edema, bronchitis, tracheobronchitis, acute lung injury (ALI), sarcoidosis of the lung, bronchiectasis, asbestosis, berylliosis, silicosis, anthracosis, Histiocytosis X, pneumotitis, smoker's lung, bronchiolitis obliterans, lung scarring due to tuberculosis and pulmonary fibrosis, pneumoconiosis, traumatic pulmonary injury, and pulmonary infections and pulmonary manifestations of connective tissue diseases, including systemic lupus erythematosus, rheumatoid arthritis, scleroderma, polymyositis and dermatomyositis.

In certain implementations, the compositions and methods disclosed herein are used to prevent, treat or alleviate one or more symptoms of a disease that causes hypoxia, such as altitude disease, anemia, a blood clot in the lung (pulmonary embolism), congenital heart defects or disease, medications that lower breathing rate (such as some narcotics and anesthetics), lung inflammation by toxic agents such as nitrogen dioxide gas, scarring in the lungs (pulmonary fibrosis) and sleep apnea.

EXAMPLES

The disclosure is further illustrated by the following examples that should not be construed as limiting. The contents of all references, patents, and published patent applications cited throughout this application, as well as the Figures, are incorporated herein by reference in their entirety for all purposes.

Example 1: Oral Administration of Elemental Magnesium and Nitrate Alleviates COVID-19 Symptoms On 21 of October 2000, a male 32 years old subject started showing COVID-19 symptoms including chest pain, fever, muscle pain, cough, shortness of breath, and low oxygen saturation (between 90-92% during various measurements). Every four hours, the subject was administered on an empty stomach two capsules. One capsule comprises 1200 mg potassium nitrate ($KNO_3$), 200 mg elemental magnesium, and 50 mg of elemental zinc, and the other capsule comprised 1000 mg citric acid (the contents of these capsules did not contain any binders fillers or excipients, only the ingredients listed above).

Within half an hour of the first administration, the subject reported great relief from shortness of breath, chest pain, breathing difficulty. His oxygen saturation level also increased from 92% to 97%. The subject's oxygen saturation was intermittently tracked for two days (Table 2). Although the subject's oxygen saturation level would start to decline within the 4 hours, taking another dose of the two capsules (one capsule with the elemental metals and nitrate, and one capsule with the citric acid) would return the subjects SpO2 to the normal range of 96%-100%. By the fourth day of taking the two aforementioned capsules every four hours, the subject reported no more symptoms of shortness of breath, chest pain, and breathing problems. In fact, he felt good enough to return to work, but remained in quarantine due to local safety protocols. By the second day of taking the two capsules every four hours, the subject's oxygen saturation levels had not fallen below normal. The subject then later tested positive for Covid-19 infection.

TABLE 2

Tracking of oxygen saturation in a subject before and after treatment.

| Day and Time | Oxygen Saturation Level Before Treatment | Oxygen Saturation Level After Treatment |
|---|---|---|
| Day 1, 5 PM | 92% | 97% |
| Day 1, 10 PM | 94% | 96% |
| Day 2, 9AM | 94% | 97% |
| Day 2, 2 PM | 95% | 96% |

Example 2: A Trial with Five Adult COVID-19 Patients Demonstrates the Treatment's Efficacy An open label case series trial performed by the FSPE Applied Bioenergetics Lab (University of Novi Sad, Lovcenska 16, Novi Sad 21000, Serbia) evaluated the effects of a composition comprising 1200 mg of potassium nitrate, 200 mg of elemental magnesium, 50 mg of elemental zinc in one capsule, and 1000 mg of citric acid co-administered in another capsule, on blood oxygen saturation level ($SpO_2$) and patient-reported outcomes in COVID-19 patients.

Five adult patients (3 males and 2 females, 37.0±4.4 years old) with COVID-19 having breathing difficulties and $SpO_2$<95% and free from other pulmonary and cardiovascular conditions were recruited for this study. The participants received the composition every 4 hours during a 48-hour monitoring period. No other treatments for an improvement in oxygen saturation level were administered during the trial. $SpO_2$ and patient-reported outcomes were evaluated at baseline (pre-intervention) and at each 4-hour time point throughout the trial.

Figure 6A:
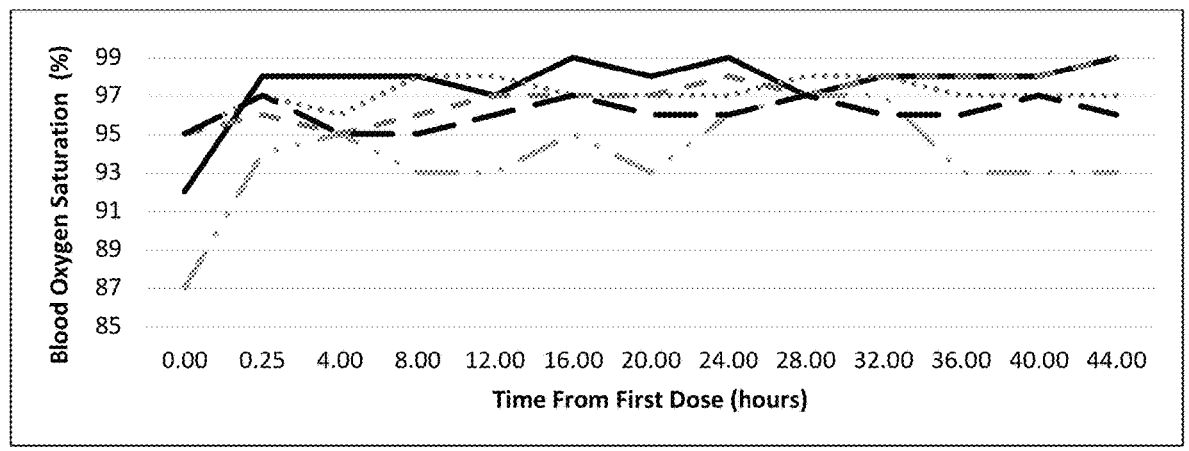
FIG. 6A depicts individual changes in oxygen saturation during the trial. Each line represents a different patient.
Figure 6B:
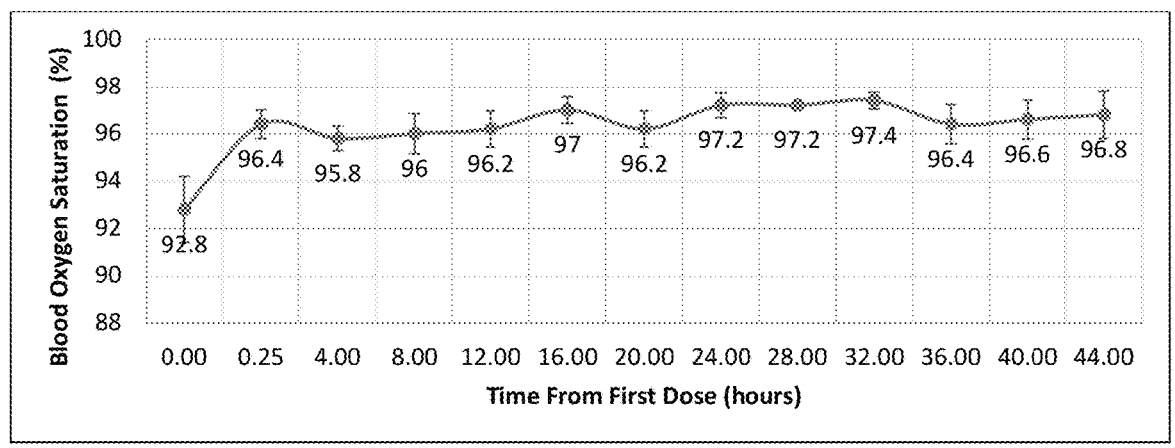
FIG. 6B depicts average blood oxygen saturation of the patients during the trial. Error bars mark the standard error.

$SpO_2$ improved immediately upon administration of the composition for all participants (increase of 1-7%, mean increase 3.6±2.7 points; 95% confidence interval from 0.3 to 7.0). $SpO_2$ remained above baseline values throughout the monitoring interval with values persisting over the threshold value (>92%) for all patients and at each time point during the 48 hours (see FIGS. 6A and 6B). If the blood oxygen saturation level falls below the threshold of 92%, a patient is advised to seek medical aid. Thus, by keeping the patients well over the threshold, it could reduce the stress in healthcare system.

No patients reported any side effects of the intervention. In addition to the improvements in blood oxygen saturation level, one patient (female, 39 years old) reported a reduction in cough, breathing difficulties, and chest pain. Another patient (male, 38 years old) reported attenuated diarrhea. A third patient (female, 35 years old) reported reduction of fatigue and headache.

Example 3: Hydrogen Gas is Formed as a Byproduct of the Reaction Between Elemental Magnesium and Citric Acid To confirm that hydrogen gas is a byproduct of the combining the elemental metal with an acid, a teaspoon of elemental magnesium powder was added to a vial containing 100 ml of water saturated with citric acid. The air on top of the vial was flammable.

Example 4: Elemental Magnesium and Nitrate Alleviate Respiratory Illness Symptoms Five subjects (male, ages 34- to 52-years old) with a respiratory illness and having $SpO_2$ less than 92% were administered a composition comprising 1200 mg of potassium nitrate, 200 mg of elemental magnesium, 50 mg of elemental zinc in one capsule, co-administered with another capsule containing 1000 mg of citric acid. Their blood oxygen saturation level was measured between 15 to 80 minutes after ingestion of the composition. Their symptoms related to the respiratory illness were also recorded before and after ingestion of the composition. Table 3 summarizes the results.

TABLE 3

Improvement of respiratory symptoms after treatment.

| Subject Age (years) | $SpO_2$ (%) Before | After | Symptoms | Alleviated Symptoms |
|---|---|---|---|---|
| 34 | 92 | 98 | Fatigue | Fatigue |
| 46 | 93 | 98 | Headache | Headache |
| 39 | 92 | 97 | Fatigue, cloudy head | Cloudy head |
| 45 | 90 | 95 | Difficulty breathing | Difficulty breathing |
| 52 | 89 | 98 | Body aches, anxiety | Anxiety |

Example 5: Oral Administration of Elemental Magnesium and Potassium Nitrate Produces NO Exhalation from the Lungs A Niox Vero machine was used to measure ambient nitric oxide and lung excreted nitric oxide in two subjects after ingesting a composition with 1000 mg potassium nitrate ($KNO_3$), 200 mg elemental magnesium in one capsule, and 1 gram citric acid co-administered in a separate capsule. The measurements showed that ingestion of the composition instantly produced nitric oxide gas and increased lung excretion of nitric oxide.

Example 6: Oral Administration of Elemental Magnesium and Nitrate Improves Blood Oxygen Levels and Alleviates Symptoms of Post-COVID-19 Lung Damage and Chronic Hypoxia A male subject (40 years old, Brazilian) was diagnosed with COVID-19 on January 25. He exhibited symptoms of fatigue, tiredness, inability to perform at exercise, inability to perform at work, inability to perform at sexual life, burnout, collapse, exhaustion, frazzle, lassitude, prostration, and weariness. The symptoms persisted after finally testing negative for COVID-19, and for months after being infected and then testing negative from the disease the subjects SpO2 levels (i.e., percentage of oxygen in his blood) as measured by a pulse oximeter were below 95%. The subject was ultimately diagnosed with acute respiratory distress syndrome (ARDS).

On June 10, the subject ingested one capsule containing 1200 mg $KNO_3$, 200 mg elemental magnesium (mesh size 60-200), and 50 mg of elemental zinc dust(mesh size 325) and a second capsule containing 1000 mg citric acid. Prior to ingesting the two capsules, his SpO2 levels, as measured by a pulse oximeter, was 91. Fifty minutes after ingestion of the two capsules, his SpO2 level, as measured by a pulse oximeter, was 97. The subject took the composition every four hours for five days. He reported a reduction of all of the symptoms related to COVID-19, and the effect lasted for the duration of the treatment.

At the end of the initial five-day dosing protocol, the subject continued to take the composition once every morning to manage the persistent COVID-19 symptoms. Even with just one maintenance dose of the described composition, the subject's SpO2 levels, as measured by a pulse oximeter, did not fall below 95% again, and all the lingering symptoms of his original COVID-19 infection had been alleviated.

Figure 5A:
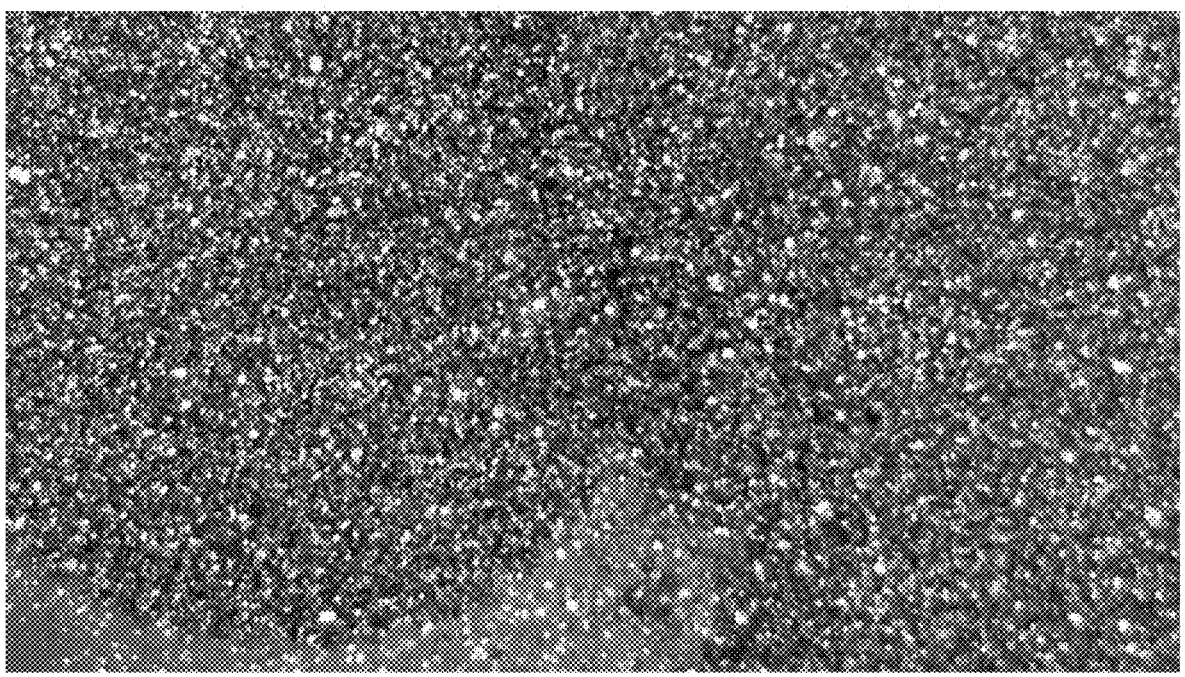
FIG. 5A depicts magnesium dust at 500× magnification.
Figure 5B:
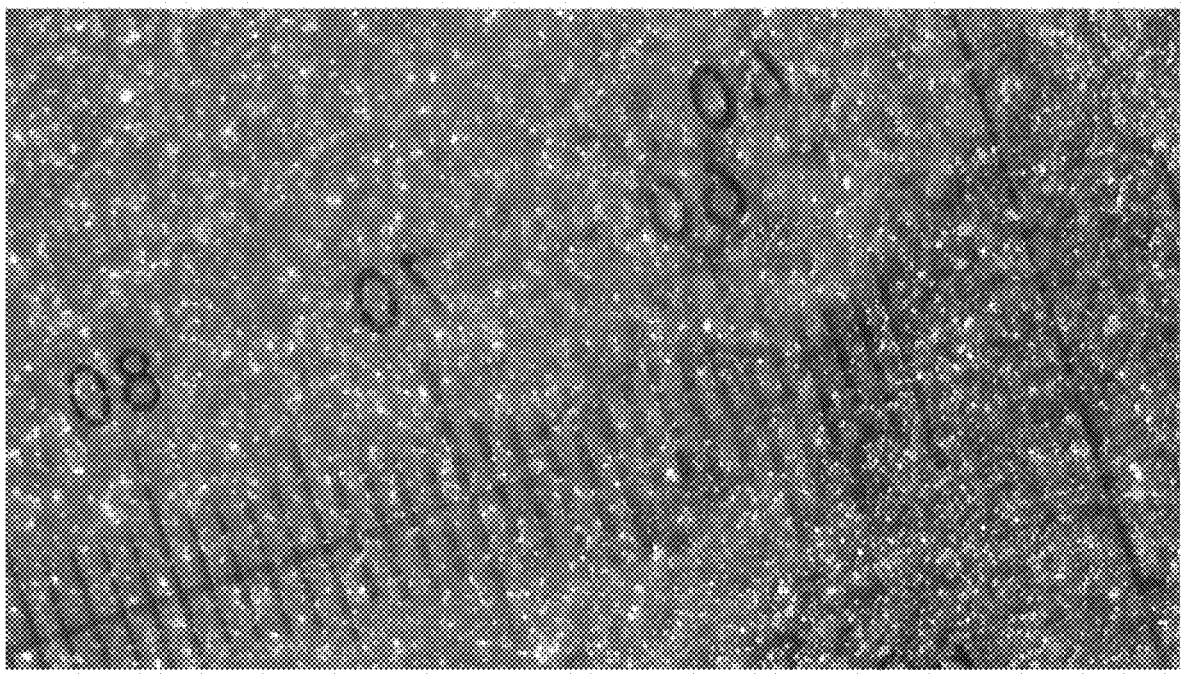
FIG. 5B depicts magnesium dust at 500× magnification with a micrometer (each indentation=0.1 mm).
Figure 5C:
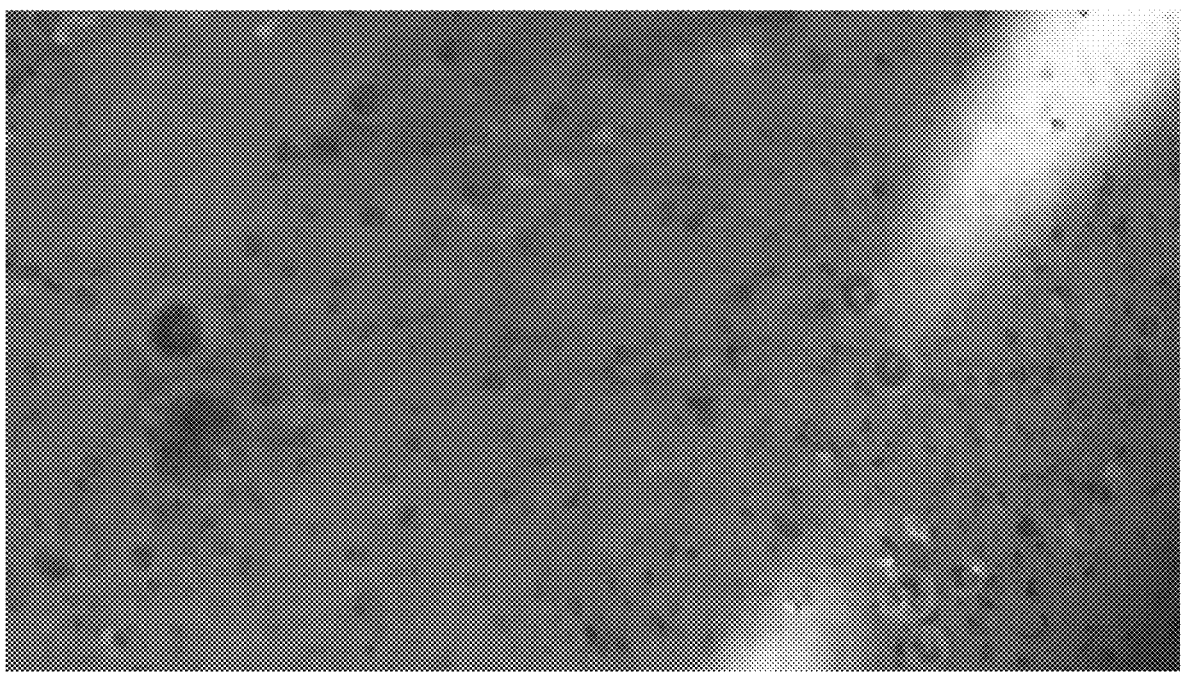
FIG. 5C depicts magnesium dust reacted with acidified water (1000 mg citric acid in 100 ml water) at 10 seconds at 500× magnification.

Example 7: Elemental Magnesium Dust Rapidly Generates NO and $NO_2$ Gas when Mixed with Potassium Nitrate in an Acid Solution A glass beaker with a volume of 100 ml containing 200 mg of elemental magnesium dust (mesh size 325 or finer; see FIGS. 5A-5C), 1200 mg $KNO_3$, and 1000 mg citric acid was mixed with 100 ml of distilled water. The beaker was placed in a sealed gas chamber (Bel-Art Secador Polystyrene Mini Desiccator Cabinet, 0.31 $ft^3$), and the gaseous contents generated were measured using probes. The $H_2$ sensor started rapidly rising and turned off due to reaching maximum measurable capacity. Table 4 summarizes the results from the NO and $NO_2$ sensors.

TABLE 4

NO and $NO_2$ measurements during the course of the reaction.

| Time | NO (ppm) | $NO_2$ (ppm) |
|---|---|---|
| Start: 16:21:45 | 0.0 | 0.0 |
| 16:22:24 | 119.4 | 4.1 |
| 16:22:27 | 194.0 | 5.7 |
| 16:22:30 | 203.2 | 8.3 |
| 16:22:34 | 228.4 | 9.0 |
| 16:22:47 | 250 | 29.2 |

The results were both surprising and unexpected. At 60 seconds after the experiment started, both the NO and $NO_2$ sensors had reached maximum measurable capacity at 250 ppm and 100 ppm respectively. These surprising results show that the mesh size of the magnesium is a very important factor for the safe use of the compositions, discoveries and inventions disclosed herein. With very small particle size the reaction takes place too fast and both NO and $NO_2$ gas rapidly reach non-therapeutic concentrations that are extremely dangerous and toxic for humans.

According to the Occupational Safety and Health Administration (OSHA), at 2 ppm $NO_2$ can trigger symptoms in asthmatic people, at 5 ppm it starts to damage the lungs, and the permissible exposure limit for $NO_2$ in homes and offices should not exceed 5 ppm (9 $mg/m^3$). However, $NO_2$ levels as low as 0.1 ppm have been shown to cause respiratory discomfort in vulnerable populations such as asthmatics. $NO_2$ at 100 ppm can kill a human if exposed for about an hour. While NO is therapeutic and safe at low concentrations, concentration of 100 ppm or higher are also outright toxic. The inventions disclosed herein allow for the first time a safe and effective method for the therapeutic delivery of NO gas with little or no adverse side effects.

Example 8: Elemental Zinc Generates NO Gas when Mixed with Potassium Nitrate in an Acid Solution An experiment similar to that described in Example 7 was performed with elemental zinc powder. Elemental zinc proved to be less reactive than elemental magnesium. The zinc powder reacted with potassium nitrate in a citric acid solution and produced lower amounts of NO and hydrogen than those observed with magnesium for over 4 hours.

Example 9: Elemental Magnesium and Nitrate Improve Blood Oxygen Levels and Reduce Coughing and Weakness Associated with Respiratory Illness Whereas an Equal Amount of Nitrate Alone has No Effect A 58-year-old male subject exhibited weakness, coughing, and a blood oxygen saturation level (SpO2) of 93%. The subject was given a capsule containing only 1200 mg of potassium nitrate. After 15 minutes, the subject's $SpO_2$ remained at 93%. For up to 4 hours after the administration of the potassium nitrate capsule, the subject's $SpO_2$ showed no signs of increase, and he exhibited no attenuation of his other symptoms. Four hours after administration of the first capsule, the subject was administered a composition comprising a capsule containing 1200 mg potassium nitrate, 200 mg elemental magnesium, and 50 mg elemental zinc and a separate capsule containing 1000 mg citric acid. Fifteen minutes after the administration of this composition, the subject's $SpO_2$ increased to 97% and remained above 95% for 4 hours. The subject also reported experiencing reduced cough and no longer felt weak.

Example 10: Elemental Magnesium Prevents Methemoglobinemia Induced by High Sodium Nitrite Poisoning Sodium nitrite is known to be poisonous at high amounts being able to oxidize hemoglobin to methemoglobin, which cannot carry oxygen, an effect similar to methemoglobinemia induced by prolonged NO gas therapy. Because of its toxicity, its utilization in therapeutics is limited only to an antidote used for cyanide poisoning. The lowest calculated lethal dose is 2.6 grams (Katabami et al., "Severe Methemoglobinemia due to Sodium Nitrite Poisoning", *Case Reports in Emergency Medicine,* 2016, Article ID 9013816, 3 pages), but there have been reported cases of severe methemoglobinemia with much lower doses, such as about 70 mg in the case of a geriatric patient with cardiovascular problems. Administration of 600 mg to an adult for the treatment of cyanide toxicity resulted in a methemoglobin level of 58% (van Heijst et al., "Therapeutic Problems in Cyanide Poisoning," *Journal of Toxicology: Clinical Toxicology,* 1987, 25(5): 383-398). Moderate-to-severe poisoning is associated with cyanosis (blueness of the skin), confusion, loss of consciousness, seizures, abnormal heart rhythms, and death. Due to the lack of observed cases of methemoglobinemia for subjects ingesting a combination of elemental metal and a source of nitrate and/or nitrite or inhaling the gas produced by the combination in an acidic solution, it was hypothesized that the exposure to hydrogen gas and/or zinc or magnesium ions could prevent the development of methemoglobinemia. Methemoglobinemia can be monitored both directly by time consuming blood test or indirectly by SpO2 measurements since methemoglobin cannot carry $O_2$ and thus higher methemoglobin levels results in lower oxygen saturation levels.

One of the inventors, having fasted overnight, ingested a capsule containing 310 mg of $NaNO_2$ and one capsule containing 1000 mg citric acid with the intention of inducing methemoglobinemia, while the other inventor monitored the conditions of the test subject inventor. After the first 15 minutes, the test subject inventor started experiencing unwanted side effects including gastrointestinal distress, dizziness, brain fog, confusion, difficulty in breathing, migraine, abnormal heart palpitations, tachycardia with a peak of 240 pulses/minute, and low SpO2 levels with a lowest reading of 91 at about 25 minutes into the experiment. Table 5 summarizes the test subject inventor's SpO2 levels and heart rate (HR) over the course of the experiment. SpO2 levels and heart rate readings were recorded and they can be found in the table below.

TABLE 5

Monitoring after administration of sodium nitrite and citric acid.

|  | Time | SpO2 | HR |
|---|---|---|---|
|  | 11:45 AM | 98 |  |
| Take 310 mg sodium nitrite and 1000 mg citric acid capsules | 11:50 AM | 98 | 181 |
|  | 11:55 AM | 98 | 221 |
|  | 12:00 PM | 96 | 240 |
|  | 12:05 PM | 95 | 121 |
|  | 12:08 PM | 91.5 | 117 |
|  | 12:10 PM | 94 | 225 |
|  | 12:15 PM | 94 | 125 |
|  | 12:20 PM | 93 | 215 |
|  | 12:25 PM | 94 | 128 |
|  | 12:30 PM | 93 | 139 |
|  | 12:35 PM | 93 | 133 |
|  | 12:40 PM | 92 | 229 |
|  | 12:45 PM | 95 | 108 |
|  | 12:50 PM | 94 | 114 |
|  | 12:55 PM | 95 | 92 |
|  | 1:00 PM | 95 | 161 |
|  | 1:05 PM | 95 | 122 |
|  | 1:10 PM | 94 | 132 |
|  | 1:15 PM | 95 | 84 |
|  | 1:20 PM | 95 | 152 |
|  | 1:25 PM | 96 | 122 |
| Take 1000 mg citric acid and elemental magnesium | 1:30 PM |  |  |
|  | 1:35 PM | 96 | 92 |
|  | 1:40 PM | 97 | 106 |

After a 48-hour washout period, the test subject inventor prepared 3 capsules each containing 1000 mg elemental magnesium powder and 3 other capsules each containing 1000 mg citric acid. Elemental magnesium powder reacts violently with the acids in a very exothermic reaction. Thus, it was unknown if the ingestion of such large quantities of elemental magnesium would be safe or even tolerable and if their reaction with a toxic dose of nitrite would be tolerable. Regardless, the test subject inventor co-ingested a capsule containing 310 mg sodium nitrite and 1000 mg elemental magnesium with 2 capsules containing 1000 mg citric acid in each capsule each (because some of the acid would be consumed by the elemental magnesium, the amount of citric acid was doubled compared to the initial dose of the first experiment). After 30 minutes and after 60 minutes, the test subject inventor ingested another 1000 mg elemental magnesium and 1000 mg citric acid in capsule form. The inventor experienced none of the unwanted side effects of the first experiment. The only side effect noticed was light-headedness, which the test subject inventor had experienced many times in past experiments and easily identified that the lightheadedness is associated with low blood pressure. The test subject inventor's SpO2 levels remained elevated compared to the first experiment, never falling below the threshold level of 95%. Table 6 summarizes the test subject inventor's SpO2 levels and heart rate (HR) over the course of the second experiment.

TABLE 6

Monitoring of test subject after administration of sodium nitrite, citric acid, and elemental magnesium.

|  | Time | SpO2 | HR |
|---|---|---|---|
| Take 1x(310 mg sodium nitrite and 100 mg elemental magnesium) and 2x(1000 mg citric acid) | 11:00 AM | 100 | 105 |
|  | 11:05 AM | 99 | 103 |
|  | 11:10 AM | 97 | 112 |
|  | 11:15 AM | 97 | 161 |
|  | 11:20 AM | 96 | 133 |
|  | 11:25 AM | 96 | 214 |
|  | 11:30 AM | 95 | 117 |
| Take 1x(310 mg sodium nitrite and 100 mg elemental magnesium) and 2x(1000 mg citric acid) | 11:31 AM |  |  |
|  | 11:35 AM | 95 | 120 |
|  | 11:40 AM | 96 | 135 |
|  | 11:45 AM | 95 | 181 |
|  | 11:50 AM | 97 | 135 |
|  | 11:55 AM | 95 | 121 |
|  | 12:00 PM | 95 | 137 |
| Take 1000 mg citric acid and elemental magnesium | 12:02 PM |  |  |
|  | 12:07 PM | 95 | 99 |
|  | 12:14 PM | 95 |  |
|  | 12:21 PM | 95 | 201 |

The test subject inventor felt completely fine 90 minutes after the experiment. The test subject's SpO2 level was in the area of 95%-97%. Thus, the administration of elemental magnesium prevented the onset of methemoglobinemia induced by ingestion of sodium nitrite.

Example 11: Elemental Magnesium and Nitrate Effectively Treat Asthma

A female subject diagnosed with asthma (71 years old, Black American) was administered one capsule containing 1200 mg KNO3, 200 mg elemental magnesium (mesh size 60-200), and 50 mg of elemental zinc and a second capsule containing 1000 mg citric acid in the mornings with a glass of cold water instead of using a preventive inhaler. The subject had tried various inhalers to treat her asthma with mixed results, but upon oral administration of the capsules, the subject experienced immediate relief of her asthma symptoms. She also started producing more sputum and started breathing better, which are signs of improvements in asthma patients. While receiving the treatment, the subject reported no side effects, including those related to traditional asthma treatments such as chest discomfort.

Example 12: Hydrogen Gas Prevents NO-Induced Methemoglobinemia

During the course of developing the described methods for producing NO for a more affordable, effective, and safe source of NO therapy, one of the inventors accidentally exposed himself both chronically and acutely to NO gas. One day after exposing himself to a high amount of ambient NO (ambient NO >80 ppm), he started experiencing symptoms of methemoglobinemia and had lung inflammation, as exhibited by SpO2 of 85%, dizziness, pain in the lungs and weakness. Since onset of symptoms, the inventor inhaled $H_2$ gas, produced by reacting elemental magnesium and citric acid in a glass of water. He also ingested 2000 mg elemental magnesium powder with water, which would generate $H_2$ gas in reaction with the HCl in his stomach. In other experiments, the inventor found that minor methemoglobinemia caused by inhalation of NO gas would be reversed by administering $H_2$ gas (as represented by SpO2 returning to normal).

His condition and SpO2 worsened throughout the day, and later that night he was admitted in the emergency room at a hospital with a recorded SpO2 of 45%. The hospital verified that the inventor developed NO-induced lung inflammation by X-rays and a CAT scan. Upon the diagnosis, blood samples were taken from the inventor to measure methemoglobin levels. To the surprise of the medical staff, no methemoglobin was detected even while the inventor had an SpO2 of 45%. A normal methemoglobin fraction is about 1%. He also never exhibited during his transfer blue skin (cyanosis) which is associated with a 3-15% methemoglobin levels. Accordingly, no methemoglobin treatment (e.g., intravenous administration of methylene blue) was administered to the inventor.

Thus, hydrogen inhalation and ingestion (via the form of an elemental metal, in this case magnesium) treated and/or alleviated NO-induced methemoglobinemia. Since atmospheric $H_2$ concentrations range around 530 ppb and this is ineffective to produce any protective effect in patients undergoing inhaled NO gas therapy, an amount greater than that, at least 10 ppm, preferable 100 ppm or more, will be needed for said protective effects. However the amount should be kept below 2000 ppm, preferably below 1500 ppm, to avoid water formation in the lungs.

Example 13: Nitric Oxide is Formed by Reacting Elemental Magnesium and Potassium Nitrate in an Acid Solution In a 1000 ml beaker, an acid solution was produced by dissolving 5 grams of citric acid in 100 ml of warm water. Elemental magnesium (200 mg) and potassium nitrate (1000 mg of) were simultaneously added to the acid solution. A FeNO by Niox machine, which can measure ambient NO levels, was used to tested whether NO gas formed from the addition of elemental magnesium and potassium nitrate into the acid solution. The room's NO levels before the experiment were 0. Soon after the addition of elemental magnesium and potassium nitrate into the acid solution, the machine recorded 200 ppb NO. More NO may have been generated, as 200 ppb is the machine's limit of detection.

Example 14: Elemental Magnesium or Elemental Zinc is Required for the Production of Nitric Oxide from Potassium Nitrate A flask containing 100 ml 0.1M HCl was put in a Bel-Art Secador Polystyrene Mini Desiccator Cabinet (0.31 cu. ft.). The contents of one capsule containing 1200 mg $KNO_3$, 200 mg elemental magnesium, and 50 mg elemental zinc and the contents of a second capsule containing 1000 mg citric acid was added to the flask. An NO sensor was placed into the desiccator cabinet. In 10 minutes, NO levels rose from 0 ppm to 6.4 ppm. Thus, theoretically, with the average stomach having a size of one liter, the amount of NO in the stomach from ingesting the two capsules would be 56 ppm.

Notably, adding 1 teaspoon of $KNO_3$ to 50 ml 25% HCl did not result in any measurable amount of NO gas.

Example 15: The Size of Elemental Magnesium Impacts the Effectiveness, Safety, and Side Effects Profile of the Compositions Administered Multiple iterations of the composition with differing mesh sizes of the elemental metal were prepared and tested in subjects to determine whether the mesh size of the elemental metal would affect the benefits and/or side effects that a subject would experience upon ingestion. Table 7 lists the formulations tested.

TABLE 7

Formulations of elemental metal evaluated in studies.

| Composition | Metal (amount in mg) | Size | Other Ingredients (amount in mg) |
|---|---|---|---|
| 1 | Mg (200 mg) | Mg beads - 5 mm in diameter | $KNO_3$ (1200 mg), citric acid (1000 mg) |
| 2 | Mg (200 mg) | Mg granules - 35 mesh | $KNO_3$ (1200 mg), citric acid (1000 mg) |
| 3 | Mg (100 mg) | Mg powder - 60-200 mesh | $KNO_3$ (310 mg), citric acid (1000 mg) |
| 4 | Mg (100 mg) | Mg dust -325 mesh | KNO3(310 mg), citric acid (1000 mg) |

The different formulations demonstrated varying effectiveness in alleviating respiratory illnesses. In some cases, the subjects experienced side effects including gastrointestinal disturbances, diarrhea, nausea, and vomiting. Adverse effects were much more common with the magnesium dust formulation than with the other formulations.

Example 16: Various Forms of Elemental Magnesium are Capable of Generating $H_2$, NO, and $NO_2$ Gases with Potassium Nitrate Three forms (and sizes) of elemental magnesium at 200 mg amount (FIG. 1) were used to compare the generation of $H_2$, NO, and $NO_2$ gas produced after mixing with 1200 mg $KNO_3$ and 1000 mg citric acid powder upon the addition of 100 ml water. Immediately after adding 100 ml distilled water at room temperature, the beaker containing the magnesium was placed in a Bel-Art Secador Polystyrene Mini Desiccator Cabinet (0.31 ft$^3$). At the beginning of the experiment with magnesium powder, granular magnesium, and magnesium beads, the sensors for $H_2$, NO, and $NO_2$ were all zero.

Figure 2A:
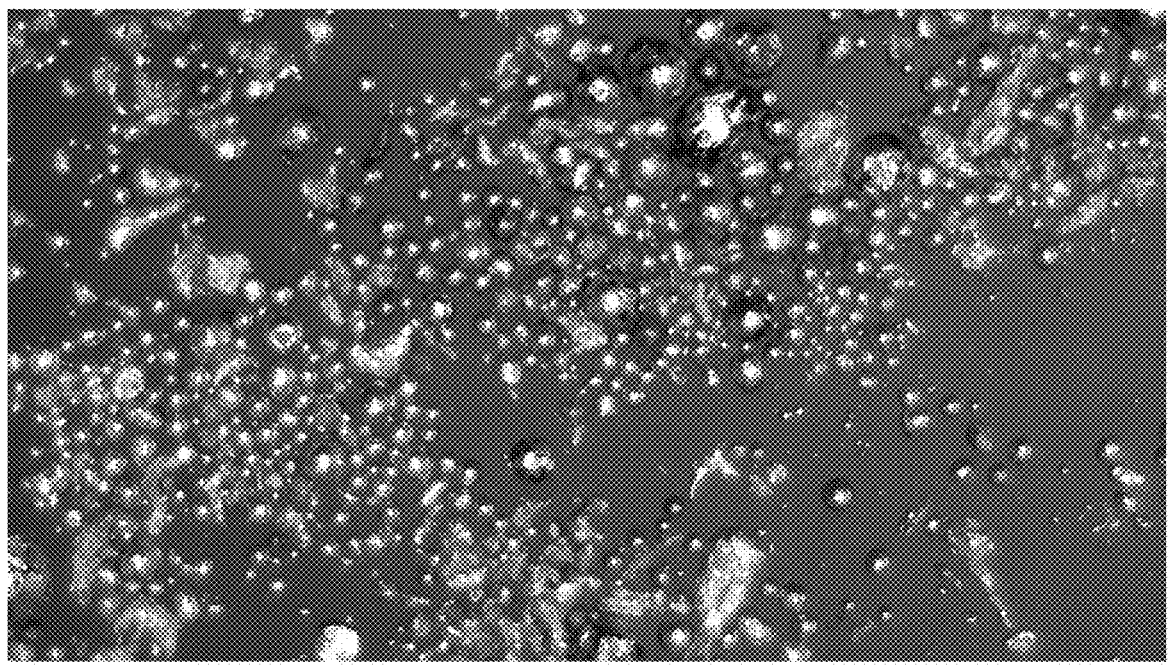
FIG. 2A depicts an image of magnesium powder at 500× magnification.
Figure 2B:
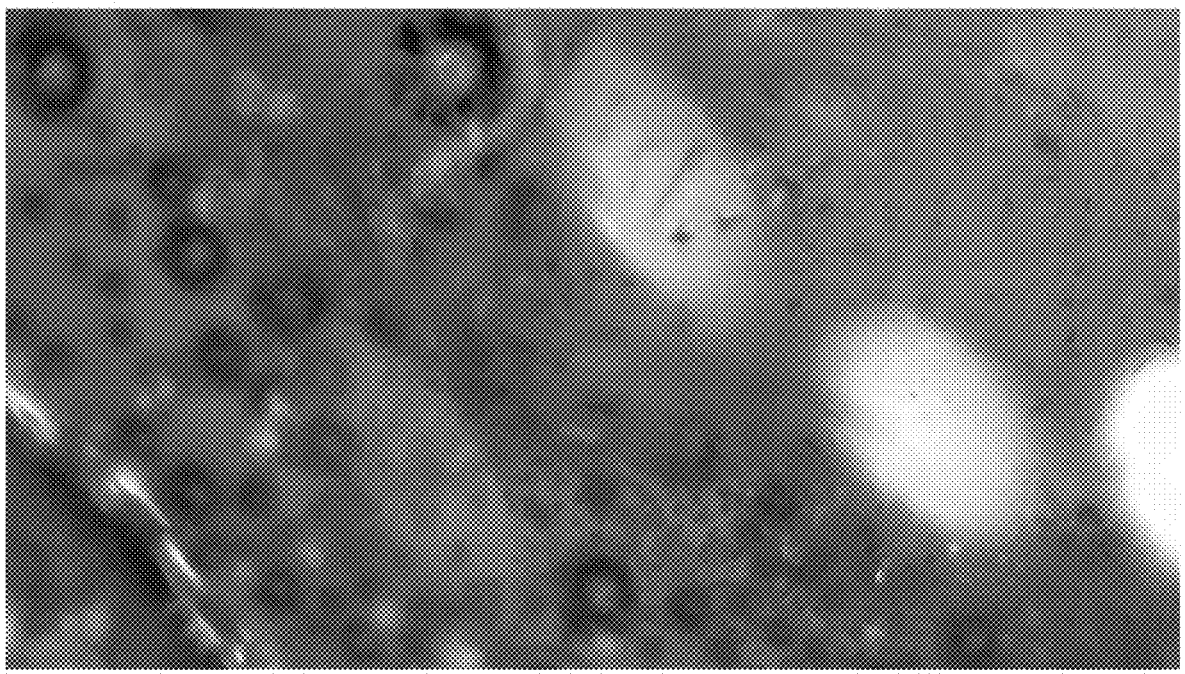
FIG. 2B depicts an image of magnesium powder reaction with acidified water (1000 mg citric acid in 100 ml water) at 10 seconds at 500× magnification.

About 90 seconds after the addition of water to the beaker with magnesium powder (60-200 mesh size) and 1200 mg $KNO_3$ and 1000 mg citric acid powder (see FIGS. 2A and 2B), the concentration of NO gas was 12.8 ppm, $NO_2$ gas was 0 ppm, and $H_2$ gas was 142 ppm. As the experiment continued, the concentration of NO and $H_2$ gases continued to rise. At 2 minutes after the water was added to the powder, the concentration of NO gas was 39.2 ppm, $H_2$ gas was 435 ppm, and $NO_2$ gas was at 0 ppm. This ratio of NO to $NO_2$ is surprising. It was previously unheard of to reach nearly 40 ppm NO gas with zero $NO_2$. At 5 minutes after the water was added to the powder, NO gas reached 49 ppm, while the $NO_2$ gas increased to 3.0 ppm. Hydrogen gas increased to over 1000 ppm (maximum detectable range of the sensor).

Figure 3A:
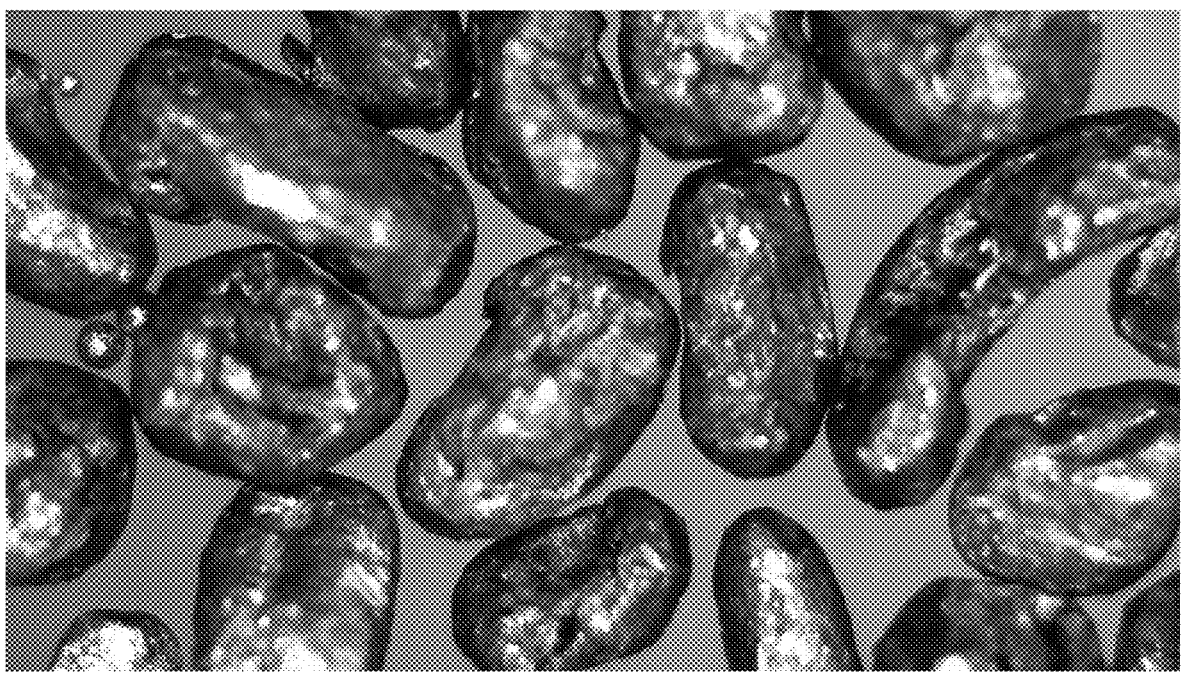
FIG. 3A depicts an image of magnesium granules at 500× magnification.
Figure 3B:
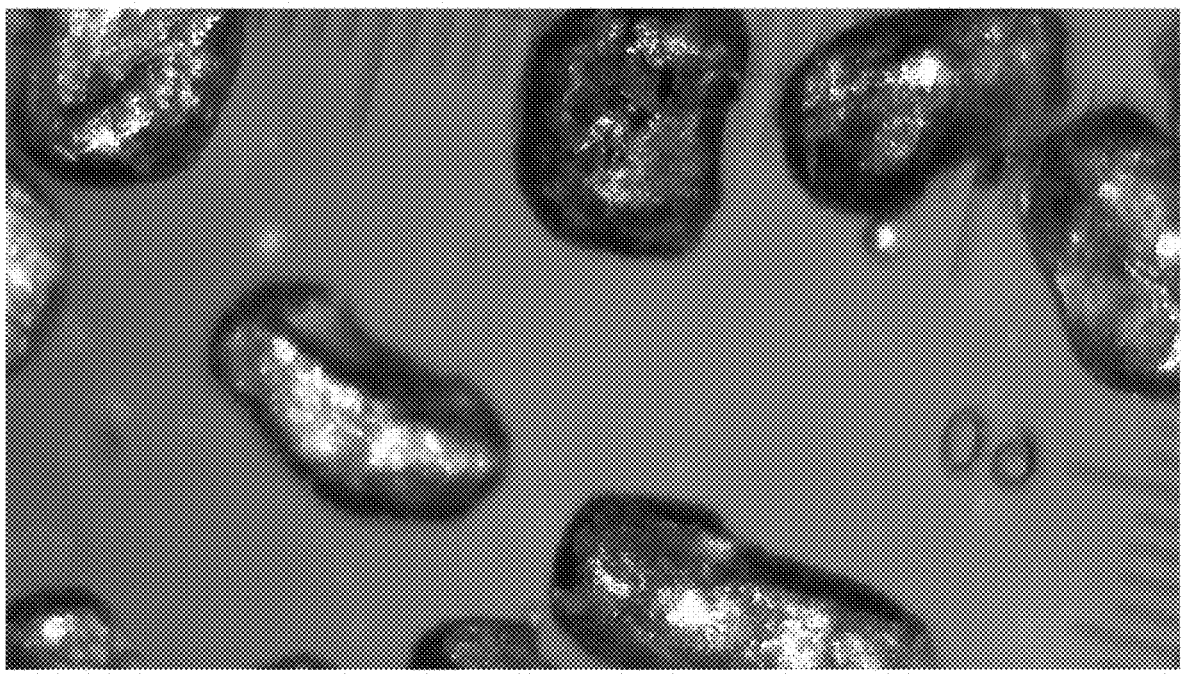
FIG. 3B depicts an image of magnesium granules at 500× magnification with a micrometer (each indentation=0.1 mm).
Figure 3C:
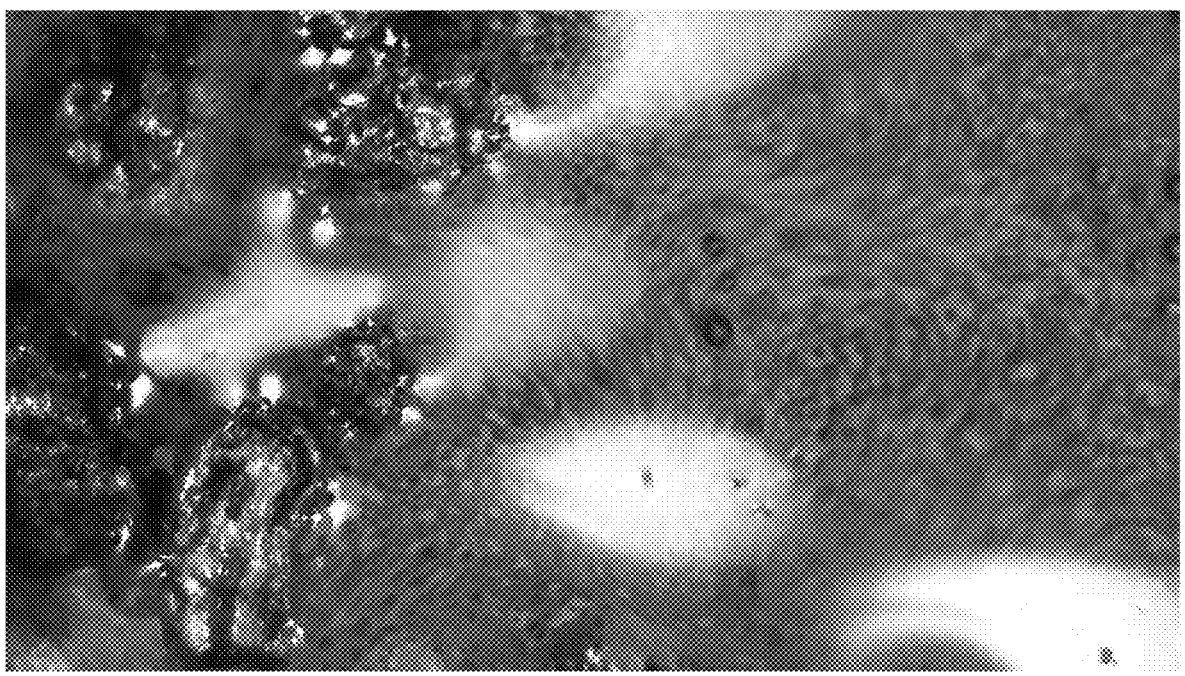
FIG. 3C depicts an image of a reaction of magnesium granules with acidified water (1000 mg citric acid in 100 ml water) after 10 seconds at 500× magnification.
Figure 4A:
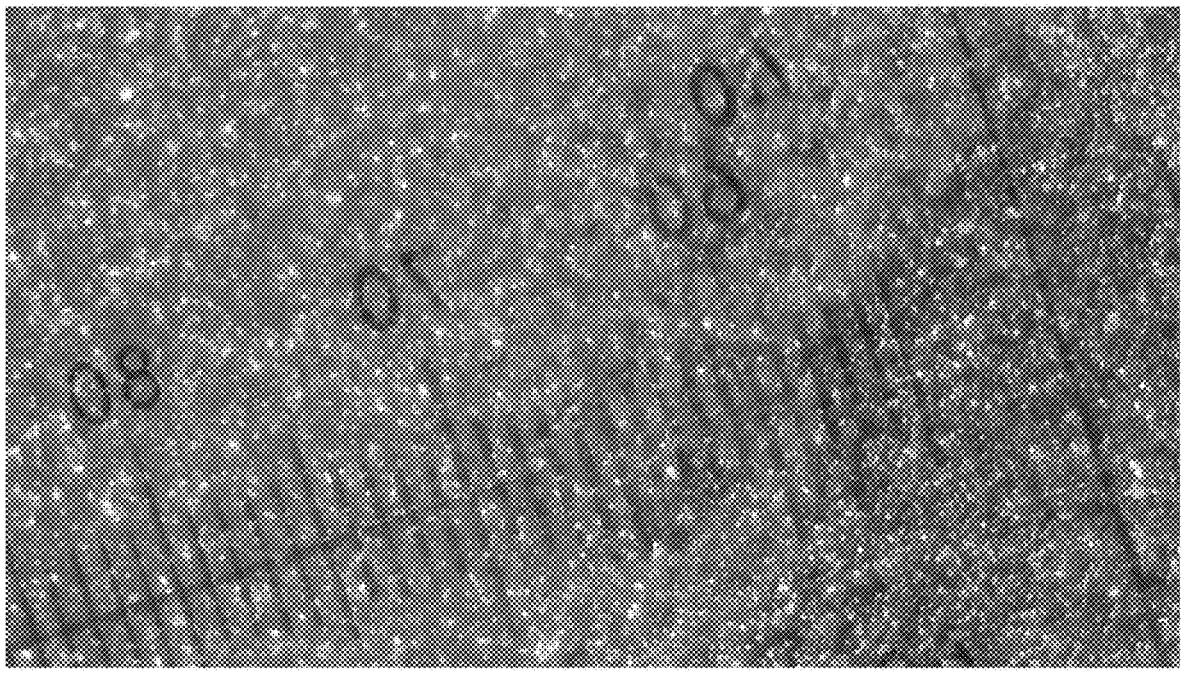
FIGS. 4A-4C present a comparison of 500× magnification views of magnesium dust (FIG. 4A), magnesium powder (FIG. 4B), and magnesium granules (FIG. 4C) via a micrometer ruler (each indentation is 0.1 mm).
Figure 4B:
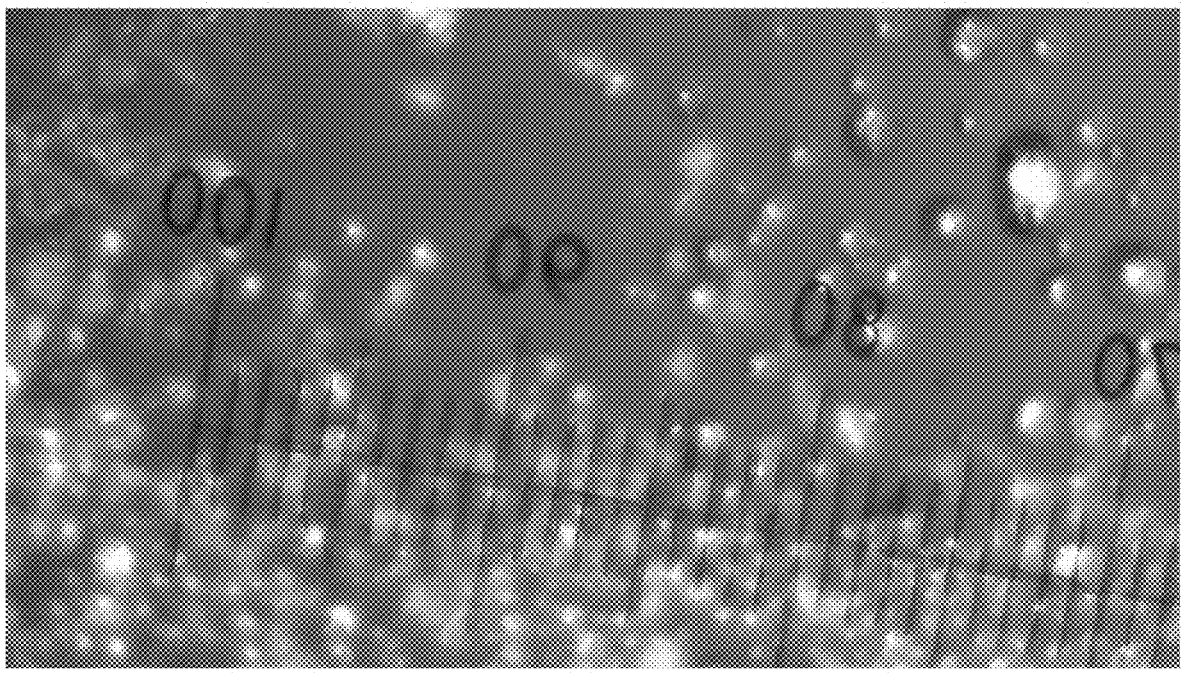
Figure 4C:
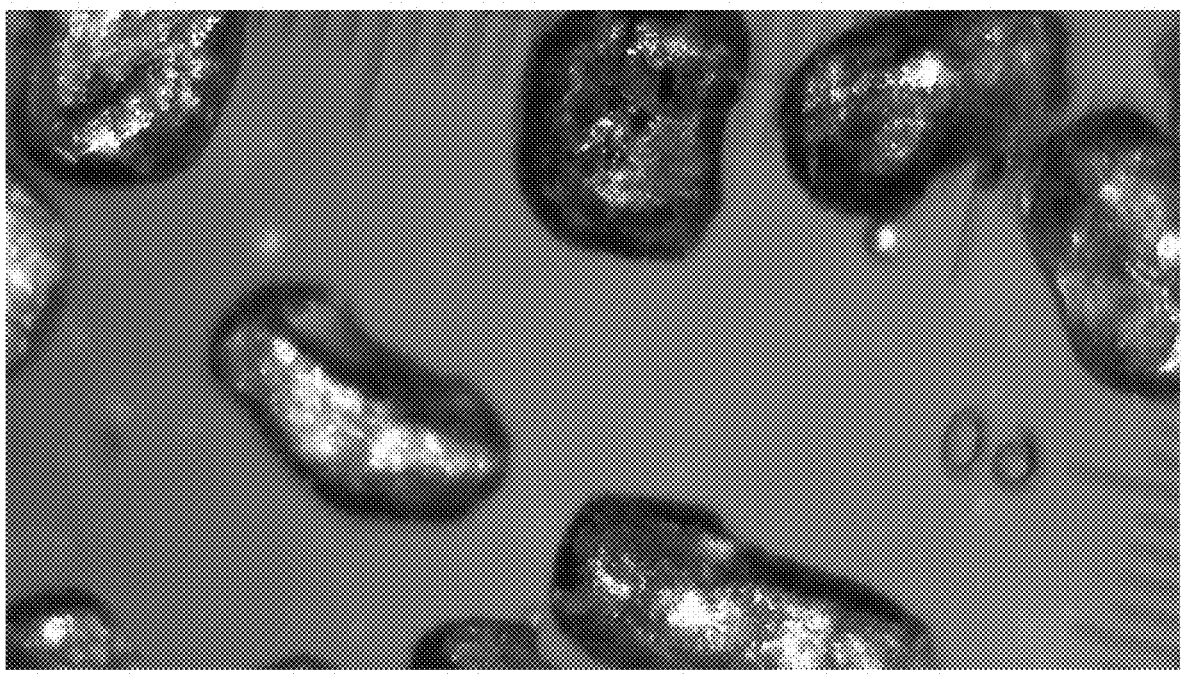

In the experiment with granular magnesium (~35 mesh size) and 1200 mg $KNO_3$ and 1000 mg citric acid powder (see FIGS. 3A, 3B, and 3C), the concentrations of NO gas, $H_2$ gas, and $NO_2$ gas at 1 minute after the addition of water were 3.8 ppm, 66 ppm, and 0 ppm, respectively. At 5 minutes after the addition of water, the sensor reading was 11.4 ppm for NO gas, 186 ppm for $H_2$ gas, and 0 ppm for $NO_2$ gas. Thus, using granular magnesium produced much less NO and $H_2$ gas with nearly 4 times less NO in the same time frame when compared with the magnesium powder.

In the experiment with magnesium beads (about 5 mm diameter) and 1200 mg $KNO_3$ and 1000 mg citric acid powder (see FIG. 1), at 1 minute and 20 seconds into the experiment, no NO gas or $NO_2$ gas were produced. At 5 minutes after the addition of water, the sensor reading for NO gas was 16.2 ppm, for $NO_2$ gas was 0 ppm, and for hydrogen 337 ppm.

Our experiments show that coproduction of $H_2$ gas with NO gas with the disclosed methods and compositions reduces or even eliminates the production of $NO_2$ gas.

Example 17: The Elemental Magnesium and Nitrate Formula Effectively Eradicates *Helicobacter pylori*

*Helicobacter pylori* is a Gram-negative, microaerophilic, spiral (helical) bacterium usually found in the stomach and the upper small intestine. *H. pylori* prevalence ranges between 85% and 95% in developing countries and between 30 and 50% in developed countries. Symptoms of active infection include G.I. pain, which usually is worse in an empty stomach, nausea, loss of appetite, frequent burping, bloating and unintentional weight loss, gastric ulcers, gastric bleeding, and irritable bowel syndrome. *H. pylori* has been associated with many respiratory disorders, including chronic obstructive pulmonary disease (COPD), bronchiectasis, asthma, lung cancer and tuberculosis. Common features of *H. pylori* infection and chronic lung diseases are chronic inflammation as well as increased immune response. Eradication of *H. pylori* is difficult and requires long administration of a combination of antibiotics (typically amoxicillin and clarithromycin) together with a PPI inhibitor (such as omeprazole) to avoid G.I. side effects from the antibiotic administration. A 50 year old woman was diagnosed positive for *H. pylori* and exhibited all the aforementioned symptoms. She has in the past been prescribed a combination of Amoxicillin (1000 mg twice per day), Clarithromycin (500 mg twice per day) and Omeprazole (20 mg twice per day) for a 30 day regimen but still tested positive for *H. pylori* after cessation of the therapy. She was prescribed by the inventor a treatment that comprised one capsule with 10 mg Sodium Nitrite, 1000 mg Potassium Nitrate and 200 mg elemental metal Magnesium 200 mg and another separate capsule that comprised 500 mg citric acid and 500 mg gallic acid. She was advised to ingest the aforementioned combination of capsules twice per day for 10 days. From day 2, she reported relief of the symptoms. After the 10 days, she tested for *H. pylori* and was found negative. Since then, many subjects that experienced chronic gastrointestinal and pain and received the specific formulation of one capsule containing 1200 mg $KNO_3$– 200 mg elemental Mg– 50 mg elemental Zn+ one capsule containing 1000 mg Citric Acid, taken twice per day and reported elimination of gastrointestinal pain that existed before their infection.

Example 18: Hydrogen Gas Produced the Formulations

It should also be noted that the inventors noticed that hydrogen, at high concentrations, can result in the formation of water that, if inhaled for prolonged times, would result in accumulation of water in a subject's lungs that could hinder oxygen absorption from the lungs. That would be an explanation for the low SpO2 the inventor suffered when he inhaled $H_2$ gas for a prolonged time to combat methemoglobinemia from NO. In a series of experiments comparing atmospheric humidity with $H_2$ concentration procured from the formulation at 30 C ambient temperature, the inventor noticed that for every about 40 ppm increase in $H_2$ concentration, the relative humidity would increase by 1% (the amount of water vapor present in air expressed as a percentage of the amount needed for saturation at the same temperature). The results of the relative humidity increase as the $H_2$ concentration increased are shown in Table 8 below.

TABLE 8

Impact of hydrogen gas on atmospheric humidity in a closed system.

| $H_2$ ppm | Atmospheric Humidity % |
|---|---|
| 0 | 44% |
| 178 | 47% |
| 322 | 48% |
| 458 | 49% |
| 526 | 50% |
| 587 | 51% |
| 617 | 52% |
| 647 | 53% |
| 676 | 54% |
| 720 | 56% |
| 754 | 57% |
| 779 | 58% |
| 801 | 59% |
| 826 | 60% |
| 858 | 61% |
| 897 | 62% |
| 1000 | 64% |

While the sensor's limit was reached at 1000 ppm, these experiments as well as the lack of any symptoms that there was water presence in the lungs (edema) in any of the subjects, show that 1000 ppm of $H_2$ concentrations are safe. It is assumed that up to 1500 ppm $H_2$ concentrations would also be safe with no noticeable $H_2O$ formation in the lungs for subjects inhaling the gases produced from the composition.

Example 19: The Significance of the Results in View of Previous Reports

Although it was shown that nitrate supplementation, in the form of sodium nitrate (Larsen F J, et al. Acta Physiol (Oxf). 2007 September; 191(1):59-66) or beetroot juice (Bailey S J, et al. J Appl Physiol (1985). 2009 October; 107(4):1144-55) could reduce oxygen consumption during exercise, supplementation with nitrate rich beetroot juice failed to increase oxygen saturation levels (SpO2) in hypoxic conditions (lower than normal blood oxygen saturation, such as in the case of ARDS patients), failed to improve SpO2, and actually increased mountain sickness severity and the sense of effort during hypoxic exercise (Rossetti G M K, et al. J Appl Physiol (1985). 2017 Oct. 1; 123(4):983-992). Furthermore, supplementation with potassium nitrate (KNO3), such as the form of nitrate utilized in the formulation by the inventors to treat COVID-19 and other respiratory and circulatory disease led to lower blood oxygen saturation (about 3% less, a significant amount) in hypoxic conditions versus the placebo (Schiffer T A, et al. Respir Physiol Neurobiol. 2013 Jan. 15; 185(2):339-48). Thus, despite the hypothesis from Dr. Lundberg, Dr. Weitzberg, and their colleagues that nitrate would increase SpO2 in hypoxia, KNO3 supplementation actually decreased SpO2 levels, and in other studies nitrate (such as that present in beetroot juice) had no effect on SpO2.

A well-known drawback of NO gas therapy is the development of methemoglobinemia (Weinberger B, et al. Toxicol Sci. 2001 January; 59(1):5-16), which is the oxidation of hemoglobin's iron rendering hemoglobin unable to carry oxygen. Methemoglobinemia can be diagnosed by a drop in the subject's oxygen saturation, which can be measured with a pulse oximeter (SpO2). Other methemoglobinemia symptoms include discoloration (e.g., pale, gray, blue) of the skin and changes in the color of the blood. Surprisingly, none of the subjects ingesting the formulations disclosed herein experienced methemoglobinemia (which would have resulted in a decrease in SpO2 levels, whereas all the subjects experienced an increase in SpO2 levels) nor was there noted any abnormal change in skin coloration. Thus, surprisingly, administration of the formula even throughout days, produced no methemoglobinemia.

Example 20: Elemental Magnesium and Nitrate Effectively Treat Interstitial Lung Disease and Related Chronic Hypoxia A 77-year-old female subject suffered from interstitial lung disease with breathing difficulties and chronic hypoxia (SpO2 less than 95%). She also experienced chronic severe coughing attacks. Because of cystitis, she was advised against ingesting the citric acid capsule of the formulation, as citric acid has been reported to worsen inflammation of the urine tract.

She was administered half a dose of the elemental metal and nitrate formulation (600 mg $KNO_3$, 100 mg elemental metal magnesium, and 25 mg elemental metal zinc in a size 0 gelatin capsule), which she swallowed with enough water on an empty stomach. Her SpO2 level was 94%. 25 minutes later her SpO2 rose to 98% while her pulse dropped from 80 to 69, indicating a more efficient transportation of oxygen and blood from the heart to the tissues. Through the course of 10 days, she kept taking the above formulation multiple times per day, resulting in a sustained increase in SpO2 levels which would remain in the normal range with a subsequent decrease in pulse rate. The subject also reported great relief from difficulty breathing and an ablation of the coughing attacks from the treatment. The subject's blood pressure was monitored after each dosing using a medical grade FDA-approved device. With the start of this treatment, the subject's blood pressure reduced and remained reduced through the course of her treatment. The patient experienced no negative side effects.

All headings are for the convenience of the reader and should not be used to limit the meaning of the text that follows the heading, unless so specified.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:

1. A method of increasing blood oxygen saturation (SpO2) in a human subject, the method comprising:
orally administering to the human subject at least one elemental metal selected from the group consisting of: elemental magnesium, elemental calcium, elemental zinc, elemental copper, and elemental iron; and
orally administering to the human subject a nitrate ($NO_3^-$), a nitrite ($NO_2^-$), or both.

2. The method of claim 1, further comprising orally administering to the human subject a pharmaceutically effective amount of an acid.

3. The method of claim 2, wherein the human subject is administered a nitrate salt and/or a nitrite salt and the human subject is administered citric acid as the acid.

4. The method of claim 3, wherein the human subject is administered potassium nitrate as the nitrate and/or potassium nitrite as the nitrite.

5. The method of claim 1, wherein the human subject has a blood oxygen saturation level (SpO2 level) of less than about 95% or less than about 92%.

6. The method of claim 5, wherein the oral administration of the at least one elemental metal and the nitrate and/or the nitrite to the human subject is repeated within 1 hour, 2 hours, 3 hours, 4 hours, 6 hours, 8 hours, 12 hours, 24 hours, 36 hours, 48 hours, 72 hours, or 96 hours of the initial oral administration.

7. The method of claim 5, wherein the human subject is orally administered the at least one elemental metal when the SpO2 level of the human subject falls below about 95% or about 92%.

8. The method of claim 1, wherein the SpO2 level of the human subject increases by at least about 1% within about 5 minutes to about 2.5 hours after the administration of the at least one elemental metal and the nitrate and/or the nitrite.

9. The method of claim 5, wherein the SpO2 of the human subject increases to at least about 95% within about 5 minutes to about 2.5 hours after of the administration of the at least one elemental metal and the nitrate and/or nitrite.

10. The method of claim 1, wherein the human subject has a condition selected from the group consisting of: SARS-CoV-2 infection, hypoxia after Coronavirus disease (COVID-19), acute respiratory distress syndrome (ARDS), post-ARDS hypoxia, pneumonia, chronic obstructive pulmonary disorder (COPD), mesothelioma, anemia, asthma, pulmonary embolism, collapsed lung, congenital heart defects or disease, pulmonary edema, high altitude sickness, interstitial lung disease, low breathing rate, lung inflammation, pulmonary fibrosis, sleep apnea, and a respiratory infection.

11. The method of claim 10, wherein the condition is a viral respiratory infection.

12. The method of claim 11, where the human subject is hypoxic.

13. The method of claim 1, wherein the human subject exhibits at least one symptom selected from the group consisting of: tissue damage, muscle aches, body aches, fatigue, sore throat, shortness of breath, difficulty breathing, chest pain, lung inflammation, cough, fever, anosmia, dysgeusia, sinus congestion, runny nose, decreased blood oxygen saturation, headache, nausea, vomiting, diarrhea, tiredness, inability to exercise, inability to work, inability to perform sexual activity, burnout, collapse, exhaustion, frazzle, lassitude, prostration, weariness, fatigue, worsening of symptoms after physical or mental activities, difficulty thinking or concentrating, cough, fast-beating or pounding heart, increased heart rate, heart failure, and acute respiratory failure.

14. The method of claim 13, wherein the tissue damage is in the brain, heart, lung and/or kidney.

15. The method of claim 14, wherein the administration of the at least one elemental metal and the nitrate and/or nitrite alleviates the at least one symptom in the human subject.

16. The method of claim 1, wherein the human subject is orally administered a composition comprising the at least one elemental metal and the nitrate and the composition comprises about 1 mg to about 2000 mg of the at least one elemental metal and about 30 mg to about 4000 mg of the nitrate.

17. The method of claim 16, wherein the composition comprises elemental magnesium and/or elemental zinc.

18. The method of claim 1, wherein the human subject is orally administered a composition comprising:
about 1200 mg potassium nitrate;
about 200 mg elemental magnesium; and
about 50 mg elemental zinc.

19. The composition of claim 18, wherein the composition further comprises about 1000 mg citric acid.

20. The method of claim 18, wherein the composition is provided in one or more capsules.

21. The method of claim 20, wherein capsules have a size of 0 or smaller.

22. The methods of claim 18, wherein the elemental metal magnesium has a mesh size of 60 to 200 and the elemental metal zinc has a mesh size of 325 or lower.

23. The method of claim 1, wherein NO is formed in the gastrointestinal tract of a patient in amounts greater than that of NO that would be formed by ingestion of a nitrate or nitrite without an elemental metal who is orally administered (i) the elemental metal and (ii) the nitrate ($NO_{3-}$), a nitrite ($NO_2^-$), or both.

24. The method of claim 1, wherein NO is formed in the stomach of a patient who is orally administered (i) the elemental metal and (ii) the nitrate ($NO_{3-}$), a nitrite ($NO_2^-$), or both.

25. The method of claim 24, wherein NO is formed at a concentration of at least 5 ppm.

26. The method of claim 24, wherein NO is formed at a concentration of at least 10 ppm.

27. The method of claim 24, wherein NO is formed at a concentration of at least 20 ppm.

28. The method of claim 24, wherein NO is formed at a concentration of at least 30 ppm.

29. The method of claim 1, wherein the at least one elemental metal is magnesium.

30. The method of claim 1, wherein the at least one elemental metal is zinc.

31. The method of claim 1, wherein the at least one elemental metal is iron.

32. The method of claim 1, wherein the at least one elemental metal is calcium.

33. The method of claim 3, wherein the human subject is administered sodium nitrate and/or sodium nitrite.

34. The method of claim 5, wherein the SpO2 of the human subject increases by at least about 1% within about 5 minutes to about 2.5 hours after of the administration of the at least one elemental metal and the nitrate and/or nitrite.

35. The method of claim 24, wherein no detectable amounts of $NO_2$ are formed.

36. The method of claim 1, wherein the at least one elemental metal and the nitrate ($NO_{3-}$) and/or nitrite ($NO_2^-$) are administered are in the form of one or more capsules.

37. The method of claim 1, wherein the at least one elemental metal and the nitrate ($NO_{3-}$) and/or nitrite ($NO_2^-$) are administered are in the form of a tablet.

38. The method of claim 1, wherein the at least one elemental metal and the nitrate ($NO_{3-}$) and/or nitrite ($NO_2^-$) are administered are in the form of a softgel.

39. The method of claim 2, wherein the at least one elemental metal and the nitrate ($NO_{3-}$) and/or nitrite ($NO_2^-$) are administered are in the form of one or more capsules and wherein in the acid is administered in the form of a separate capsule.

40. The method of claim 2, wherein the at least one elemental metal and the nitrate ($NO_{3-}$) and/or nitrite ($NO_2^-$) are administered are in the form of a tablet and wherein in the acid is administered in the form of a separate tablet.

41. The method of claim 2, wherein the at least one elemental metal and the nitrate ($NO_{3-}$) and/or nitrite ($NO_2^-$) are administered are in the form of a softgel and wherein in the acid is administered in the form of a separate softgel.

* * * * *

UNITED STATES PATENT AND TRADEMARK OFFICE
CERTIFICATE OF CORRECTION

PATENT NO. : 12,156,886 B2
APPLICATION NO. : 17/525841
DATED : December 3, 2024
INVENTOR(S) : Ronald Kramer et al.

Page 1 of 1

It is certified that error appears in the above-identified patent and that said Letters Patent is hereby corrected as shown below:

In the Claims

In Claim 1, Column 34, Line 22, "($NO_{3\text{-}}$)" should read -- ($NO_3^-$) --.

In Claim 13, Column 35, Line 13, "or pounding heart, increased heart rate" should read -- or pounding heart, hypertension, increased heart rate --.

In Claim 23, Column 35, Line 46, "($NO_{3\text{-}}$)" should read -- ($NO_3^-$) --.

In Claim 24, Column 35, Line 50, "($NO_{3\text{-}}$)" should read -- ($NO_3^-$) --.

In Claim 36, Column 36, Line 28, "($NO_{3\text{-}}$)" should read -- ($NO_3^-$) --.

In Claim 37, Column 36, Line 31, "($NO_{3\text{-}}$)" should read -- ($NO_3^-$) --.

In Claim 38, Column 36, Line 34, "($NO_{3\text{-}}$)" should read -- ($NO_3^-$) --.

In Claim 39, Column 36, Line 38, "($NO_{3\text{-}}$)" should read -- ($NO_3^-$) --.

In Claim 40, Column 36, Line 43, "($NO_{3\text{-}}$)" should read -- ($NO_3^-$) --.

In Claim 41, Column 36, Line 47, "($NO_{3\text{-}}$)" should read -- ($NO_3^-$) --.

Signed and Sealed this
Twenty-fifth Day of February, 2025

Coke Morgan Stewart
*Acting Director of the United States Patent and Trademark Office*